United States Patent [19]
Reuschling et al.

[11] Patent Number: 5,650,417
[45] Date of Patent: Jul. 22, 1997

[54] SUBSTITUTED PYRIDINES, THEIR PREPARATION, AND THEIR USE AS PESTICIDES AND FUNGICIDES

[75] Inventors: Dieter Bernd Reuschling, Butzbach; Adolf Heinz Linkies, Frankfurt; Volkmar Wehner, Sandberg; Rainer Preuss, Hofheim; Wolfgang Schaper, Diedorf; Harald Jakobi, Frankfurt; Peter Braun, Nieder-Olm; Werner Knauf, Eppstein; Burkhard Sachse, Kelkheim; Anna Waltersdorfer, Frankfurt; Manfred Kern, Lörzweiler; Peter Lümmen, Niedernhausen; Werner Bonin, Kelkheim, all of Germany

[73] Assignee: Hoechst Schering AgrEvo GmbH, Berlin, Germany

[21] Appl. No.: 305,214

[22] Filed: Sep. 12, 1994

[30] Foreign Application Priority Data

Sep. 14, 1993 [DE] Germany .................. 43 31 181.4

[51] Int. Cl.$^6$ .................. C07D 213/30; C07D 213/32; C07D 213/38; A61K 31/44
[52] U.S. Cl. .................. 514/352; 546/312; 546/304; 546/298; 546/301; 546/14; 546/15; 546/194; 546/296; 546/303; 546/297; 514/318; 514/63; 514/348; 514/349; 514/345; 514/350; 504/100; 540/470; 540/481; 540/575
[58] Field of Search .................. 546/304, 15, 14, 546/312; 514/352, 63, 278; 504/100

[56] References Cited

U.S. PATENT DOCUMENTS

| | | | |
|---|---|---|---|
| 3,682,936 | 8/1972 | Tarba | 260/297 R |
| 4,786,317 | 11/1988 | Mengel et al. | 71/94 |
| 4,835,279 | 5/1989 | Lee et al. | 546/315 |

FOREIGN PATENT DOCUMENTS

| | | |
|---|---|---|
| 0182769 | 5/1986 | European Pat. Off. . |
| 0476607 | 3/1992 | European Pat. Off. . |
| 0480258 | 4/1992 | European Pat. Off. . |
| 3731626 | 3/1989 | Germany . |
| WO93/05050 | 3/1993 | WIPO . |

OTHER PUBLICATIONS

Bernardi, R. et al. *Chemical Abstract Services*, CA 113:23630 (1990).

*Primary Examiner*—Matthew V. Grumbling
*Assistant Examiner*—King Lit Wong
*Attorney, Agent, or Firm*—Curtis, Morris & Safford, P.C.

[57] ABSTRACT

Substituted pyridines, their preparation, and their use as pesticides and fungicides.

The invention relates to compounds of the formula

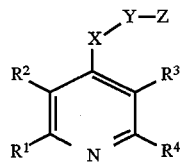

and to salts thereof in which 1, 2, 3 or 4 of the radicals $R^1$, $R^2$, $R^3$ and $R^4$ are an aliphatic, alicyclic or araliphatic radical bonded by a —O—$CH_2$— or —O—CO—, and the remaining ones of these radicals are H, halogen or an aliphatic or aromatic radical, X is O, S or optionally substituted imino, Y is a bond or a bivalent radical and Z is an aromatic radical or optionally substituted cycloalkyl or cycloalkenyl. The invention furthermore relates to processes for their preparation and to their use as pesticides, in particular as insecticides, acaricides and fungicides.

5 Claims, No Drawings

SUBSTITUTED PYRIDINES, THEIR PREPARATION, AND THEIR USE AS PESTICIDES AND FUNGICIDES

The invention relates to novel substituted 4-amino- and 4-hydroxypyridines, to processes for their preparation, and to their use as pesticides, in particular as insecticides, acaricides and fungicides.

It has already been disclosed that certain substituted 4-amino- and 4-hydroxypyridines have a fungicidal, acaricidal and insecticidal activity (cf. WO 93/05050). However, the biological activity of these compounds is not satisfactory in all fields of application, in particular when low application rates and concentrations are used.

Novel substituted 4-amino- and 4-hydroxypyridines of the formula 1, which are biologically active, have now been found.

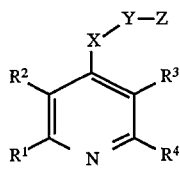

I

The invention therefore relates to compounds of the formula 1 and to salts thereof, in which (1) the number x of the radicals $R^1$, $R^2$, $R^3$ and $R^4$, which are identical or different, is selected from the group consisting of
R—O—$CH_2$—,
R—O—CO—,
halo($C_1$–$C_4$)alkoxymethyl,
halo($C_1$–$C_4$)alkenyloxymethyl,
halo($C_1$–$C_4$)alkoxycarbonyl,
halo($C_1$–$C_4$)alkenyloxycarbonyl
and cyano;
and x is 1, 2, 3 or 4;
and the remaining 4-x radicals $R^1$, $R^2$, $R^3$ and $R^4$, which are identical or different, are selected from the group consisting of
($C_1$–$C_4$)alkyl,
($C_2$–$C_4$)alkenyl,
($C_1$–$C_4$)alkoxy,
($C_2$–$C_4$)alkenyloxy,
halo($C_1$–$C_4$)alkyl,
halo($C_2$–$C_4$)alkenyl,
halo($C_1$–$C_4$)-alkoxy,
halo($C_2$–$C_4$)alkenyloxy,
($C_1$–$C_4$)alkylthio,
($C_1$–$C_4$)alkylsulfinyl,
($C_1$–$C_4$)alkylsulfonyl,
aryl,
substituted amino,
halogen and hydrogen;
R ($C_1$–$C_{10}$)alkyl,
($C_2$–$C_{10}$)alkenyl,
($C_2$–$C_{10}$)alkynyl,
($C_3$–$C_8$)cycloalkyl or aralkyl;
Aryl is as defined below under (5a);
Arylkyl is aryl($C_1$–$C_4$)alkyl;

(2) X is O, S, NH, NR or NOR and R is as defined above under (1).

(3) Y—Z together is a ($C_5$–$C_{12}$) hydrocarbon radical which is unbranched or branched and in which one or more, preferably up to three, $CH_2$ can be replaced by heteroatom groups, such as O, $NR^5$, S, SO, $SO_2$ or $SiR^6R^7$, in which $R^5$ is hydrogen, ($C_1$–$C_4$)alkyl or ($C_1$–$C_4$)acyl, and $R^6$ and $R^7$, which are identical or different, independently of one another are ($C_1$–$C_4$) alkyl, phenyl or substituted phenyl, this ($C_5$–$C_{12}$) hydrocarbon radical with the abovementioned variations which are possible (replacement by heteroatom radical(s)) optionally being substituted by one or more, preferably up to three, identical or different selected radicals from the series consisting of
($C_1$–$C_7$)alkyl,
($C_2$–$C_4$)alkenyl,
($C_2$–$C_4$)alkynyl,
($C_3$–$C_7$)cycloalkyl,
($C_3$–$C_7$)cycloalkenyl,
halogen,
halo($C_1$–$C_4$)alkyl,
halo($C_1$–$C_4$)alkoxy,
hydroxyl and
($C_1$–$C_4$)acyl; or, if not embraced by the above definitions, (4) Y is a bond or a bivalent hydrocarbon radical having 1 to 6 carbon atoms which is substituted by one or more, preferably up to three, identical or different radicals selected from the series consisting of
($C_1$–$C_7$)alkyl,
($C_2$–$C_4$)alkenyl,
($C_3$–$C_7$)alkynyl,
($C_3$–$C_7$)cycloalkyl,
($C_3$–$C_7$)-cycloalkenyl,
halogen,
halo($C_1$–$C_4$)alkyl,
halo($C_1$–$C_4$)alkoxy,
hydroxyl and
($C_1$–$C_4$)acyl; and (5) Z is
(a) aryl, O-aryl or aryl($C_1$–$C_4$)alkyl, where aryl is a phenyl group which is optionally substituted by one or more, preferably up to five, in particular up to three, identical or different radicals selected from the series consisting of
halogen,
($C_3$–$C_8$)cycloalkyl,
($C_3$–$C_8$)cycloalkenyl,
phenoxy,
substituted phenoxy,
phenylthio,
substituted phenylthio,
phenyl,
substituted phenyl,
$NO_2$,

acetoxy,
hydroxyl,
cyano,
$SiR^9R^{10}R^{11}$,
O-$SiR^9R^{10}R^{11}$,
$NR^{12}R^{13}$,
$S(O)R^{14}$,
$SO_2R^{14}$,
($C_1$–$C_{12}$)alkyl,
($C_2$–$C_{12}$)alkenyl,
($C_1$–$C_{12}$)alkoxy and $(C_1-C_{12})$alkylthio; and $R^8$ is $(C_1-C_7)$alkyl, halo$(C_1-C_7)$alkyl, $(C_3-C_7)$cycloalkyl, halo$(C_3-C_7)$cycloalkyl, $(C_1-C_7)$alkoxy, phenyl or substituted phenyl;

$R^9$, $R^{10}$ and $R^{11}$ are identical or different and independently of one another are $(C_1-C_4)$alkyl, phenyl and/or substituted phenyl;

$R^{12}$ and $R^{13}$ are identical or different and independently of one another are hydrogen, $(C_1-C_4)$alkyl and/or $(C_1-C_4)$acyl;

$R^{14}$ is $(C_1-C_{10})$alkyl, phenyl or substituted phenyl; and, if appropriate, one or more, preferably up to three, $CH_2$ groups in $(C_1-C_{12})$alkyl, $(C_2-C_{12})$alkenyl, $(C_1-C_{12})$alkoxy and $(C_1-C_{12})$alkylthio are replaced by CO and/or heteroatoms or heteroatom groups, such as O, S, SO, $SO_2$, $NR^5$ or $SiR^6R^7$;

$R^5$, $R^6$ and $R^7$ are as defined above under (3); it being possible for the $(C_1-C_{12})$alkyl radical, the $(C_1-C_{12})$alkoxy radical and the $(C_1-C_{12})$alkylthio radical, with or without the abovementioned variations (replacement by heteroatom radical(s) or CO) to be furthermore substituted by one or more, preferably up to three—in the case of halogen up to the maximum number of radicals—identical or different radicals which follow, selected from the series consisting of halogen, halo$(C_1-C_4)$alkoxy, hydroxyl, $(C_3-C_8)$cycloalkyl, $(C_3-C_8)$cycloalkenyl, $(C_1-C_4)$acyl, phenoxy, substituted phenoxy, phenyl, substituted phenyl, phenylthio and substituted phenylthio; or (b) $(C_3-C_8)$cycloalkyl or $(C_5-C_8)$cycloalkenyl, it being possible for a $CH_2$ group of the carbocycle to be replaced by $NR^{15}$;

$R^{15}$ is phenyl or substituted phenyl and the $(C_3-C_8)$cycloalkyl or $(C_5-C_8)$cycloalkenyl radical is optionally substituted by one or more, preferably up to three—in the case of halogen up to the maximum number of—identical or different radicals selected from the series consisting of $(C_1-C_{18})$alkyl,
$(C_2-C_{18})$alkenyl,
$(C_1-C_{12})$alkoxy,
$(C_2-C_{12})$acyl,
$(C_1-C_{12})$alkyloxycarbonyl,
$SiR^9R^{10}R^{11}$,
$NR^{16}R^{17}$,
hydroxyl,
oxo,
halogen,
aryl,
$(C_1-C_{18})$alkanediyl,
$(C_1-C_{18})$alkanediyldioxy,
$(C_1-C_{13})$alkyloximino,
Aryl$(C_1-C_4)$alkyloximino and
$(C_2-C_{18})$alkylidene and, in the abovementioned $(C_1-C_{18})$, $(C_2-C_{18})$, $(C_1-C_{12})$, $(C_2-C_{12})$ and $(C_1-C_{13})$ hydrocarbon radicals one or more, preferably up to three, $CH_2$ groups can be replaced by heteroatoms or heteroatom groups, such as O, $NR^5$ or $SiR^6R^7$, in which $R^5$, $R^6$ and $R^7$ are as defined under (3) and, moreover, 3 to 8, preferably 3 to 6, carbon atoms and, if appropriate, heteroatom radicals of these hydrocarbon radicals, can form a ring and these hydrocarbon radicals, with or without the variations (replacement by heteroatom radical(s) and/or ring formation) can optionally be substituted by one or more, preferably up to three—in the case of halogen up to the maximum number of—identical or different radicals selected from the series consisting of halogen, haloalkyl, cycloalkyl, acyl, phenoxy, substituted phenoxy, phenyl, substituted phenyl, phenylthio and substituted phenylthio;

$R^9$, $R^{10}$, $R^{11}$ and aryl are as defined under (5 a); and $R^{16}$ and $R^{17}$ are identical or different and independently of one another are hydrogen, $(C_1-C_6)$alkyl, $(C_1-C_6)$alkoxy, $(C_1-C_4)$acyl, $(C_3-C_6)$cycloalkyl, phenyl and substituted phenyl.

In the above formula 1, "halogen" is to be understood as meaning a fluorine, chlorine, bromine or iodine atom, preferably a fluorine, chlorine or bromine atom, in particular a fluorine or chlorine atom;

the term "alkyl" is to be understood as meaning an unbranched or branched hydrocarbon radical, such as, for example, the methyl, ethyl, propyl, 1-methylethyl, 1-methylpropyl, 2-methylpropyl or 1,1-dimethylethyl radical, the pentyl, 2-methylbutyl or 1,1-dimethylpropyl radical, the hexyl, heptyl, octyl or 1,1,3,3-tetramethylbutyl radical, the nonyl, decyl, undecyl or dodecyl radical and the like;

the terms "alkenyl" and "alkynyl" are to be understood as meaning unsaturated radicals derived from their alkyl radicals;

the term "cycloalkyl" preferably a cyclopropyl, cyclobutyl, cyclopentyl, cyclohexyl, cycloheptyl or cyclooctenyl group;

the term "alkoxy" is to be understood as meaning an alkoxy group whose hydrocarbon radical is as defined under the term "alkyl";

the term "cycloalkoxy" is to be understood as meaning a cycloalkyl group whose hydrocarbon radical is as defined under "cycloalkyl";

the term "alkylthio" is to be understood as meaning an alkylthio group whose hydrocarbon radical is as defined under the term "alkyl";

the term "haloalkyl" is to be understood as meaning an alkyl group mentioned under the term "$(C_1-C_4)$alkyl" in which one or more hydrogen atoms are replaced by the abovementioned halogen atoms, preferably chlorine or fluorine, such as, for example, the trifluoromethyl group, the 2,2,2-trifluoroethyl group, the chloromethyl, fluoromethyl, difluoromethyl or 1,1,2,2-tetrafluoroethyl group (the same applies analogously to "haloalkenyl");

the term "haloalkoxy" is to be understood as meaning a haloalkoxy group whose halogenated hydrocarbon radical is as defined under the term "haloalkyl";

the prefix "halo" means that one, more or all hydrogen atoms in these radicals are replaced by halogen atoms, and this also applies to other radicals which are not mentioned here individually;

"substituted phenyl" is to be understood as meaning a phenyl radical having one or more, preferably up to three, identical or different substituents selected from the series consisting of halogen, $(C_1-C_4)$alkyl, halo$(C_1-C_4)$alkyl, hydroxy$(C_1-C_4)$alkyl, $(C_1-C_4)$alkoxy, halo$(C_1-C_4)$alkoxy, phenoxy, phenyl, nitro, hydroxy, cyano, $(C_1-C_4)$alkanoyl, benzoyl, $(C_1-C_4)$alkanoyloxy, $(C_1-C_4)$alkoxycarbonyl;

"substituted amino" is to be understood as meaning an amino group which is substituted by one or two $(C_1-C_4)$alkyl groups or a $(C_1-C_4)$alkanoyl group;

a "bivalent hydrocarbon radical" is to be understood as meaning a radical derived from n-alkanes or n-alkenes by removal of in each case one hydrogen atom from both terminal carbon atoms of the chain, such as methylene, ethanediyl, trimethylene or tetramethylene; and "acyl" is to be understood as meaning, in particular, an alkanoyl radical, such as acetyl, propionyl or butyryl, or an alkyloxycarbonyl radical.

What has been said above applies analogously to homologs and the radicals derived therefrom.

The substituents on the cycloalkyl or cycloalkenyl radicals defined under (5b) can be in the cis or trans position relative to Y; the cis position is preferred. If only one substituent is present, it should be in cyclohexyl, preferably in the 4-position and the cis configuration.

Preferred compounds of the formula I and salts thereof are those in which (1) the number x of the radicals $R^1$, $R^2$, $R^3$ and $R^4$, which are identical or different, is selected from the group consisting of
R—O—$CH_2$—,
R—O—CO—,
halo($C_1$–$C_4$)alkoxymethyl,
halo($C_1$–$C_4$)alkenyloxymethyl,
halo($C_1$–$C_4$)alkoxycarbonyl,
halo($C_1$–$C_4$)alkenyloxycarbonyl and cyano;
and x is 1, 2, 3 or 4;
and the remaining 4-x radicals $R^1$, $R^2$, $R^3$ and $R^4$, which are identical or different, are selected from the group consisting of
($C_1$–$C_4$)alkyl,
($C_2$–$C_4$)alkenyl,
($C_1$–$C_4$)alkoxy,
($C_2$–$C_4$)alkenyloxy,
halo($C_1$–$C_4$)alkyl,
halo($C_2$–$C_4$)alkenyl,
halo($C_1$–$C_4$)alkoxy,
halo($C_2$–$C_4$)alkenyloxy,
halogen and hydrogen;
R is ($C_1$–$C_7$)alkyl,
($C_2$–$C_7$)alkenyl,
($C_2$–$C_7$)alkynyl or
($C_3$–$C_6$)cycloalkyl;

(2) X is O, S, NH, NR or NOR;

(3) Y—Z together is as defined above and is optionally substituted by one or more, preferably up to three, identical or different radicals selected from the series consisting of
($C_1$–$C_7$)alkyl,
halogen,
halo($C_1$–$C_4$)alkyl,
halo($C_1$–$C_4$)alkoxy, and
($C_1$–$C_4$)acyl; or,
if not embraced by the above definitions;

(4) Y is a bond or a bivalent hydrocarbon radical having 1 to 6 carbon atoms which is substituted by one or more, preferably up to three, identical or different radicals selected from the series consisting of
($C_1$–$C_7$)alkyl,
halogen,
halo($C_1$–$C_4$)alkyl and
halo($C_1$–$C_4$)alkoxy; and (5) Z is
(a) aryl, O-aryl or aryl($C_1$–$C_4$)alkyl, where aryl is a phenyl group which is optionally substituted by one or more, preferably up to five, in particular up to three, identical or different radicals selected from the series consisting of
halogen,
($C_3$–$C_8$)cycloalkyl,
($C_3$–$C_8$)cycloalkenyl,
phenoxy,
substituted phenoxy,
phenyl,
substituted phenyl,

$SiR^9R^{10}R^{11}$,
O—$SiR^9R^{10}R^{11}$,
$NR^{12}R^{13}$,
($C_1$–$C_{12}$)alkyl,
($C_2$–$C_{12}$)alkenyl and
($C_1$–$C_{12}$)alkoxy; and
$R^8$ is ($C_1$–$C_7$)alkyl, halo($C_1$–$C_7$)alkyl, ($C_5$–$C_6$)cycloalkyl, ($C_1$–$C_7$)alkoxy, phenyl or substituted phenyl;
$R^9$, $R^{10}$ and $R^{11}$ are identical or different and independently of one another are ($C_1$–$C_4$)alkyl, phenyl and/or substituted phenyl;
$R^{12}$ and $R^{13}$ are identical or different and independently of one another are hydrogen, ($C_1$–$C_4$)alkyl and/or ($C_1$–$C_4$)acyl;
and, if appropriate, one or more, preferably up to 3, $CH_2$ groups in ($C_1$–$C_{12}$)alkyl, ($C_2$–$C_{12}$)alkenyl and ($C_1$–$C_{12}$)alkoxy are replaced by CO and/or heteroatoms or heteroatom groups such as O, S, SO, $SO_2$, $NR^5$ or $SiR^6R^7$;
$R^5$, $R^6$ and $R^7$ are as defined above under (3); it being possible for the ($C_1$–$C_{12}$)alkyl radical and the ($C_1$–$C_{12}$)alkoxy radical, with or without the above-mentioned variations (replacement by heteroatom radical(s)) to be additionally substituted by one or more, preferably up to three—in the case of halogen up to the maximum number of radicals—identical or different radicals which follow, selected from the series consisting of halogen, halo($C_1$–$C_4$)alkoxy, ($C_3$–$C_6$)cycloalkyl, ($C_1$–$C_4$)acyl, phenoxy, substituted phenoxy, phenyl and substituted phenyl; or halogen is F or Cl;

(b) ($C_3$–$C_6$)cycloalkyl or ($C_5$–$C_8$)cycloalkenyl, it being possible for a $CH_2$ group of the carbocycle to be replaced by $NR^{15}$;
$R^{15}$ is phenyl or substituted phenyl and the ($C_3$–$C_8$)cycloalkyl or ($C_5$–$C_8$)cycloalkenyl radical is optionally substituted by one or more, preferably up to three—in the case of halogen up to the maximum number of—identical or different radicals selected from the series consisting of
($C_1$–$C_{18}$)alkyl,
($C_2$–$C_{18}$)alkenyl,
($C_1$–$C_{12}$)alkoxy,
($C_2$–$C_{12}$)acyl,
($C_1$–$C_{12}$)alkyloxycarbonyl,
$SiR^9R^{10}R^{11}$,
hydroxyl,
oxo,
halogen,
aryl,
($C_1$–$C_{18}$)alkanediyl,
($C_1$–$C_{18}$)alkanediyldioxy,
($C_1$–$C_{13}$)alkyloximino, aryl($C_1$–$C_4$)alkyloximino and ($C_2$–$C_{18}$)alkylidene and one or more, preferably up to three, $CH_2$ groups in the abovementioned ($C_1$–$C_{18}$), ($C_2$–$C_{18}$), ($C_1$–$C_{12}$), ($C_2$–$C_{12}$) and ($C_1$–$C_{13}$)hydrocarbon radicals can be replaced by heteroatoms or heteroatom groups, such as O, $NR^5$ or $SiR^6R^7$, $R^5$, $R^6$ and $R^7$ being as defined under (3) and, moreover, 3 to 6 carbon atoms and, if appropriate, heteroatom radicals of these hydrocarbon radicals can form a ring and these hydrocarbon radicals, with or without the variations (replacement by heteroatom radical(s) and/or ring formation) are optionally substituted by one or more, preferably up to three—in the case of halogen up to the maximum number of—identical or different radicals selected from the series consisting of halogen, haloalkyl, cycloalkyl, acyl, phenoxy, substituted phenoxy, phenyl and substituted phenyl; and $R^9$, $R^{10}$, $R^{11}$ and aryl are as defined under (5 a).

Particularly preferred are therefore compounds of the formula I and the salts thereof in which (1) the number x of the radicals $R^1$, $R^2$, $R^3$ and $R^4$, which are identical or different, is selected from the group consisting of
R—O—$CH_2$—,
R—O—CO—,
halo($C_1$–$C_4$)alkoxymethyl,
halo($C_1$–$C_4$)alkenyloxymethyl,
halo($C_1$–$C_4$)alkoxycarbonyl,
halo($C_1$–$C_4$)alkenyloxycarbonyl
and cyano;

and x is 1, 2, 3 or 4;

and the remaining 4-x radicals $R^1$, $R^2$, $R^3$ and $R^4$, which are identical or different, selected from the group consisting of
($C_1$–$C_3$)alkyl,
($C_2$–$C_3$)alkenyl,
($C_1$–$C_3$)alkoxy,
($C_2$–$C_3$)alkenyloxy,
halo($C_1$–$C_3$)alkyl,
halo($C_2$–$C_9$)alkenyl,
halo($C_1$–$C_3$)alkoxy,
halo($C_2$–$C_3$)alkenyloxy,
halogen and hydrogen;

R is ($C_1$–$C_5$)alkyl,
($C_2$–$C_5$)alkenyl or
($C_3$–$C_6$)cycloalkyl;

(2) X is O or NH;

(3) Y—Z together is a ($C_5$–$C_{12}$) hydrocarbon radical which is unbranched or branched and in which one or more, preferably up to three, $CH_2$ can be replaced by heteroatom groups such as O, $NR^5$ or $SiR^6R^7$, where $R^5$ is ($C_1$–$C_4$)acyl, and $R^6$ and $R^7$, which are identical or different, independently of one another are ($C_1$–$C_4$) alkyl, phenyl or substituted phenyl, this ($C_5$–$C_{12}$) hydrocarbon radical with the abovementioned variations which are possible (replacement by heteroatom radical(s)) optionally being substituted by one or more, preferably up to three, identical or different radicals selected from the series consisting of
($C_1$–$C_5$)alkyl,
fluorine, chlorine,
halo($C_1$–$C_4$)alkyl and
halo($C_1$–$C_3$)alkoxy;
or, if not embraced by the above definitions, (4) Y is a bond or a bivalent hydrocarbon radical having 1 to 6 carbon atoms which is substituted by one or more, preferably up to three, identical or different radicals selected from the series consisting of
($C_1$–$C_5$)alkyl,
fluorine, chlorine,
halo($C_1$–$C_4$)alkyl and
halo($C_1$–$C_3$)alkoxy; and (5) Z is (a) aryl or O-aryl, where aryl is a phenyl group which is optionally substituted by one or more, preferably up to five, in particular up to three, identical or different radicals selected from the series consisting of
halogen,
($C_3$–$C_6$)cycloalkyl,
phenoxy,
substituted phenoxy,
phenyl,
substituted phenyl,
$SiR^9R^{10}R^{11}$,
O—$SiR^9R^{10}R^{11}$,
($C_1$–$C_6$)alkyl and
($C_1$–$C_7$)alkoxy; and
$R^9$, $R^{10}$ and $R^{11}$ are identical or different and independently of one another are ($C_1$–$C_4$)alkyl, phenyl and/or substituted phenyl;

and, if appropriate, one or more, preferably up to three, $CH_2$ groups in ($C_1$–$C_6$)alkyl and ($C_1$–$C_7$) alkoxy are replaced by heteroatoms or heteroatom groups, such as O, S, $NR^5$ or $SiR^6R^7$;

$R^5$, $R^6$ and $R^7$ are as defined above under (3); it being possible for the ($C_1$–$C_6$)alkyl radical and the ($C_1$–$C_7$) alkoxy radical, with or without the abovementioned variations (replacement by heteroatom radical(s)) additionally to be substituted by one or more, preferably up to three, in the case of halogen up to the maximum number of radicals, identical or different of the following radicals selected from the series consisting of: halogen ($C_3$–$C_6$)cycloalkyl, phenoxy, substituted phenoxy, phenyl and substituted phenyl; and halogen is fluorine or bromine; or (b) ($C_3$–$C_6$)cycloalkyl, where a $CH_2$ group of the carbocycle can be replaced by $NR^{15}$;

$R^{15}$ is phenyl or substituted phenyl and the ($C_3$–$C_8$) cycloalkyl radical is optionally substituted by one or more, preferably up to three—in the case of halogen up to the maximum number of—identical or different radicals selected from the series consisting of
($C_1$–$C_{12}$)alkyl,
($C_2$–$C_{18}$)alkenyl,
($C_1$–$C_{12}$)alkoxy,
($C_2$–$C_{12}$)acyl,
($C_1$–$C_{12}$)alkyloxycarbonyl,
$SiR^9R^{10}R^{11}$,
hydroxyl,
oxo,
halogen,
aryl,
($C_1$–$C_{18}$)alkanediyl,
($C_1$–$C_{18}$)alkanediyldioxy,
($C_1$–$C_{18}$)alkyloximino,
aryl($C_1$–$C_4$)alkyloximino and ($C_2$–$C_{12}$)alkylidene and one or more, preferably up to three, $CH_2$ groups in the abovementioned ($C_1$–$C_{12}$), ($C_2$–$C_{12}$) and ($C_1$–$C_8$)hydrocarbon radicals can be replaced by heteroatoms or heteroatom groups, such as O, $NR^5$ or $SiR^6R^7$, where $R^5$, $R^6$ and $R^7$ are as defined under (3) and, moreover, 3 to 6 carbon atoms and/or heteroatom radical(s) of these hydrocarbon radicals can form a ring, and these hydrocarbon radicals, with or without the variations (replacement by heteroatom radical(s) and/or ring formation) are optionally substituted by one or more, preferably up to three—in the case of halogen up to the maximum number of—identical or different radicals selected from the series consisting of halogen, haloalkyl, cycloalkyl, acyl, phenoxy, substituted phenoxy, phenyl and substituted phenyl; and $R^9$, $R^{10}$, $R^{11}$ and aryl are as defined under (5 a).

The present invention relates to the compounds of the formula 1 in the form of the free base of an acid addition salt. Acids which can be used for salt formation are inorganic acids, such as hydrochloric acid, hydrobromic acid, nitric acid, sulfuric acid, phosphoric acid or organic acids, such as formic acid, acetic acid, propionic acid, malonic acid, oxalic acid, fumaric acid, adipic acid, stearic acid, oleic acid, methanesulfonic acid, benzenesulfonic acid or toluenesulfonic acid.

Some of the compounds of the formula 1 have one or more asymmetric carbon atoms. Racemates and diastereomers can therefore occur. The invention embraces the pure isomers as well as their mixtures. The mixtures of diastereomers can be separated into the components by customary methods, for example by selective crystallization from suitable solvents or by chromatography. Racemates can be resolved by customary methods to give the enantiomers, for example by salt formation with an optically active acid, resolution of the diastereomeric salts and liberation of the pure enantiomers by means of a base.

The invention furthermore relates to a process for the preparation of compounds of the formula 1 which comprises reacting compounds of the formula 2

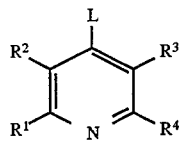

2 in which $R^1$, $R^2$, $R^3$ and $R^4$ are as defined above and L is a leaving group, with suitable amines, alcohols, phenols or mercaptans, or, for forming compounds of the formula 1 in which Z is as defined under (5b), hydrogenating those compounds of the formula 1 in which $R^1$, $R^2$, $R^3$, $R^4$, X and Y are as defined above and Z is an unsaturated carbocyclic radical which is substituted as defined for cycloalkyl or cycloalkenyl under (5b), preferably a phenyl radical which is substituted this way, and, if appropriate, converting the resulting compounds of the formula 1 into a salt thereof.

The above-described substitution reaction is known in principle. The leaving group can be varied within wide limits and can be, for example, a halogen atom, such as fluorine, chlorine, bromine or iodine, or alkylthio, such as methylthio or ethylthio, or alkanesulfonyloxy, such as methanesulfonyloxy, trifluoromethanesulfonyloxy or ethanesulfonyloxy, or arylsulfonyloxy, such as benzenesulfonyloxy or toluenesulfonyloxy, or alkylsulfonyl, such as methylsulfonyl or ethylsulfonyl, or arylsulfonyl, such as phenylsulfonyl or toluenesulfonyl.

The compounds of the formula 2 can be prepared by known methods [for example J.Med., Chem. 32, 1970 (1989), J. Org. Chem. .29 776 (1964), J. Prakt. Chem. 331, 369 (1989), J. Org. Chem. 14, 97 (1949), Chem. Ber. 74, 11111 (1941)]. Preferred compounds 2 which are used for the preparation of the compounds 1 are those in which L=Cl.

The reactions with alcohols and mercaptans are carried out in the presence of a strong base, such as sodium hydride, potassium hydride or potassium tert-butylate, in an inert aprotic solvent, such as DMF, NMP, DMSO, THF, dioxane or sulfolane, at a temperature between 0° and 80° C.; if alcoholates are reacted, it may also be advantageous to use the corresponding alcohol as a solvent.

The conditions for the reactions of 2 with amines depend on the substituents $R_1$ to $R_4$ in 2 and on the structure of the amines employed; if the radicals $R_1$ to $R_4$ in 2 are inert, 2 can be reacted with an excess of amine with or without solvent at temperatures between 80° and 200° C. to give 1. The excess of amine can be reduced and the temperature can be lowered if acidic catalysts, such as phenol [J. Amer. Chem. Soc. 73, 2623 (1951)] or salts, such as triethylammonium chloride or ammonium chloride, are used. Examples of suitable solvents are DMF, N,N-dimethylacetamide, DMSO, NMP, dioxane, diethylene glycol dimethyl ether, triethylene glycol dimethyl ether, sulfolane, toluene, chlorobenzene or xylene. Mixtures of the abovementioned solvents can also be used.

If one or more radicals of $R^1$ to $R^4$ in 2 are an RO function, then amines give poor yields of 1 or other undesired reaction products when using the abovementioned methods; exceptions are the reactions with anilines and O-alkyl- or O-aralkyl-hydroxylamines, which give the products 3 and 4 (R' is a substituent of the phenyl).

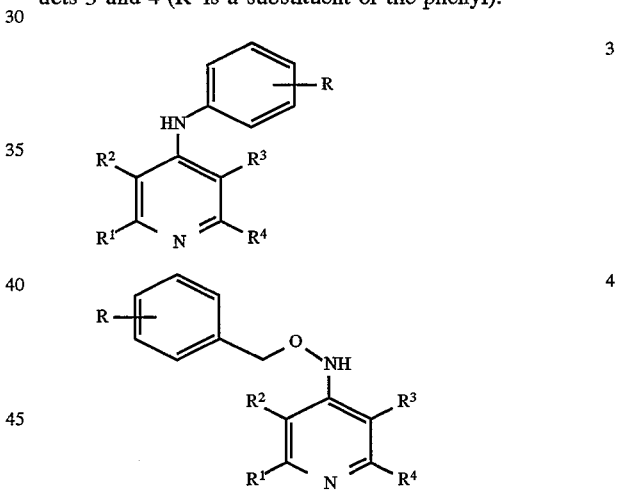

The compounds of the formula 3 can be hydrogenated catalytically by known methods [for example F. Zymalkowski, Katalytische Hydrierungen [Catalytic Hydrogenation Reactions], p. 191, Enke Verlag, Stuttgart 1965] to give compounds of the formula 1 (Diagram 1).

Diagram 1:

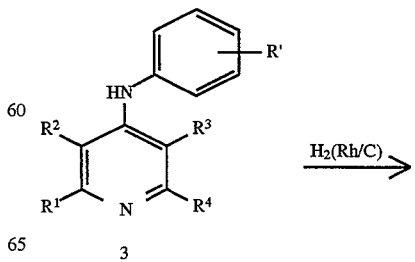

3

Diagram 1:

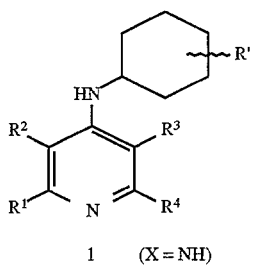

1   (X = NH)

The resulting cis/trans mixtures can be separated by crystallization or chromatography.

The compounds of the formula 4 are suitable intermediates for preparing a broad range of compounds of the formula 1 in which X=NH (Diagram 2)

Diagram 2:

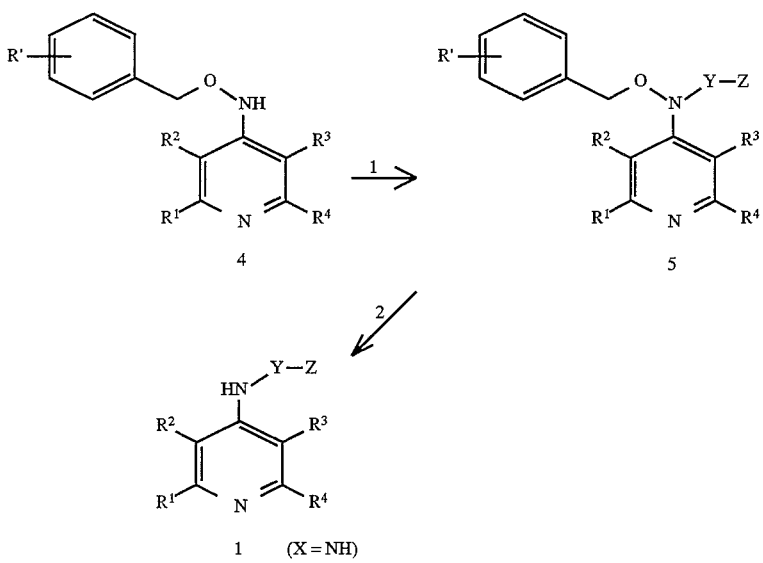

At level 1, the products of formula 4 are reacted selectively on the nitrogen substituent in the 4-position of the pyridine ring with alkylating agents of the formula L—Y—Z in the presence of bases, such as sodium hydride or potassium tert-butylate, to give 5; in formula L—Y—Z, L is halogen or R—$SO_3$, Y is as defined above (with the exception of aryl) and Z is as above. If sterically uniform alkylating agents are used it is also possible to obtain sterically uniform reaction products in this manner. Solvents which are employed in this reaction are, for example, DMF, DMSO, THF, dimethoxyethane, dioxane, diethylene glycol dimethyl ether, sulfolane or toluene. Mixtures of the above-mentioned solvents can also be used. At level 2, the compounds of formula 5 are converted reductively to the compounds of the formula 1 using known methods [R. Huisgen et al. B. 101, 2559 (1968) C. H. Rayburn, W. R. Harlau, H. R. Haumer Am. Soc. 72, 1721 (1950)].

The amines, alcohols and alkylating agents employed are accessible by methods known from the literature.

The alcohols can be prepared, for example, by reducing a carbonyl group with a suitable reducing agent, for example a complex metal hydride or, in the case of an aldehyde or ketone, also with hydrogen and a hydrogenation catalyst.

Other possibilities are the reaction of an organometal compound with a carbonyl group or an oxirane. To synthesize cyclohexanol derivatives, suitable substituted phenols can also be reacted with hydrogen in the presence of a hydrogenation catalyst.

The amines can be prepared, for example, by reduction of an oxime or a nitrile with a suitable reducing agent, for example a complex metal hydride or hydrogen in the presence of a hydrogenation catalyst, reductive amination or Leuckart-Wallach reaction of an aldehyde or ketone, or Gabriel reaction of an alkyl halide or alkyl tosylate. To synthesize cyclohexylamine derivatives, suitable substituted anilines can also be reacted with hydrogen in the presence of a hydrogenation catalyst.

The compounds of the formula 1 according to the invention are distinguished by an outstanding fungicidal activity. Fungal pathogens which have already penetrated the plant tissue can be controlled successfully in a curative manner. This is particularly important and advantageous in the case of those fungal diseases which can no longer be controlled effectively with the otherwise customary fungicides once infection has taken place. The spectrum of action of the claimed compounds embraces a range of economically important phytopathogenic fungi, such as, for example, *Phytophthora infestans, Plasmopara viticola,* but also *Erysiphe graminis* and *Pyrenophora teres.*

The compounds according to the invention are also suitable for use in industrial fields, for example as a wood preservative, a preservative, in sealants, in paints, in cooling lubricants for metalworking or as preservatives in drilling and cutting oils.

The invention also relates to compositions which contain the compounds of the formula 1 in addition to suitable formulation auxiliaries. The compositions according to the invention generally contain 1 to 95% by weight of the active substances of the formula 1.

They can be formulated in different ways, depending on the prevailing biological and/or chemical-physical parameters. The following are therefore suitable as possible formulations: wettable powders (WP), emulsifiable concentrates (EC), aqueous dispersions on an oil or water base (SC), suspoemulsions (SC), dusts (DP), seed-dressing agents, granules in the form of water-dispersible granules (WG), ULV formulations, micro-capsules, waxes or baits.

These individual types of formulation are known in principle and are described, for example, in: Winnacker-Küchler, "chemische Technologie [Chemical Technology]", Volume 7, C. Hauser Verlag Munich, 4th Edition 1986; van Falkenberg, "Pesticides Formulations", Marcel Dekker N.Y., 2nd Ed. 1972 to 73; K. Martens, "Spray Drying Handbook", 3rd Ed. 1979, G. Goodwin Ltd. London.

The formulation auxiliaries required, such as inert materials, surfactants, solvents and other additives, are equally known and are described, for example, in: Watkins, "Handbook of Insecticide Dust Diluents and Carrier", 2nd Ed., Darland Books, Caldwell New Jersey; H. V. Olphen, "Introduction to Clay Colloid Chemistry", 2nd Ed., J. Wiley & Sons, New York ; Marschen, "Solvents Guide", 2nd Ed., Interscience, New York 1950; McCutcheon's "Detergents and Emulsifiers Annual", MG Publ. Corp., Ridgewood New York ; Sisley and Wood, "Encyclopedia of Surface Active Agents", Chem. Publ. Co. Inc., New York 1964; Sch önfeldt, "Grenzflächenaktive Äthylenoxidaddukte [Surface-Active Ethylene Oxide Adducts]", Wiss. Verlagsgesell., Stuttgart 1976; Winnacker-Kechler, "Chemische Technologie [Chemical Technology]", Volume 7, C. Hauser Verlag Munich, 4th Edition 1986.

Based on these formulations, combinations with other pesticidally active substances, fertilizers and/or growth regulators can also be prepared, for example in the form of a ready mix or a tank mix.

Wettable powders are preparations which are uniformly dispersible in water and which, in addition to a diluent or inert substance, also contain wetting agents, for example polyoxethylated alkylphenols, polyoxethylated fatty alcohols, alkylsulfonates or alkylphenolsulfonates and dispersants, for example sodium ligninsulfonate, sodium 2,2'-dinaphthylmethane-6,6'-bisulfonate, sodium dibutyl-naphthalenesulfonate or else sodium oleylmethyl taurinate besides the active substance. Emulsifiable concentrates are prepared by dissolving the active substance in an organic solvent, for example butanol, cyclohexanone, dimethylformamide, xylene or else higher-boiling aromatics or hydrocarbons with an addition of one or more emulsifiers. Emulsifiers which can be used are, for example, the following:

calcium alkylarylsulfonates, such as calcium dodecylbenzenesulfonate, or nonionic emulsifiers, such as fatty acid polyglycol esters, alkylaryl polyglycol ethers, fatty alcohol polyglycol ethers, propylene oxide-ethylene oxide sorbitan fatty acid esters, polyoxyethylene sorbitan fatty acid esters or polyoxyethylene sorbital esters.

Dusts are obtained by grinding the active substance with finely divided solid substances, for example talc, natural clays, such as kaolin, bentonite or pyrophyllite, or diatomaceous earth. Granules can be prepared either by spraying substance onto adsorptive, granulated inert material or by applying active substance concentrates to the surface of carriers, such as sand, kaolinites or granulated inert material, by means of binders, for example polyvinyl alcohol, sodium polyacrylate or else mineral oils. Suitable active substances can also be granulated in the manner which is customary for the preparation of fertilizer granules, if desired in the form of a mixture with fertilizers.

In wettable powders, the concentration of active substance is, for example, approximately 10 to 90% by weight, the remainder to 100% by weight is composed of conventional formulation auxiliaries. In the case of emulsifiable concentrates, the active substance concentration can be approximately 5 to 80% by weight. Formulations in the form of dusts usually contain 5 to 20% by weight. In the case of granules, the active substance content depends partly on whether the active compound is in liquid or solid form, on which compound is present in the liquid or solid form and on which granulation auxiliaries, fillers and the like are used.

Besides, the abovementioned formulations of active substances optionally contain the adhesives, wetting agents, dispersants, emulsifiers, penetrants, solvents, fillers or carriers which are conventional in each case.

For use, the concentrates, which are in commercially available form, are, if appropriate, diluted in the customary manner, for example using water in the case of wettable powders, emulsifiable concentrates, dispersions and in the case of some microgranules.

Preparations in the form of dust and granulated preparations as well as sprayable solutions are conventionally not diluted any further with other inert substances prior to use.

The application rate required varies with external conditions, such as temperature, humidity and the like. It can vary within wide limits, for example between 0.005 and 10.0 kg/ha or more of active ingredient, but is preferably between 0.01 and 5 kg/ha.

The active substances according to the invention in their commercially available formulations can be used either by themselves or in combination with other fungicides which are known from the literature.

The following products may be mentioned, for example, as fungicides which are known from the literature which can be combined according to the invention with the compounds of formula 5: aldimorph, andoprim, anilazine, BAS 480F, BAS 490F, benalaxyl, benodanil, benomyl, binapacryl, bitertanol, bromuconazole, buthiobate, captafol, captan, carbendazim, carboxin, CGA 173506, chlobenzthiazone, chlorthalonil, cymoxanil, cyproconazole, cyprofurem, dichlofluanid, dichlomezin, diclobutrazole, diethofencarb, difenconazole (CGA 169374), difluconazole, dimethirimol, dimethomorph, diniconazole, dinocap, dithianon, dodemorph, dodine, edifenfos, ethirimol, etridiazole, fenarimol, fenfuram, fenpiclonil, fenpropidin, fenpropimorph, fentin acetate, fentin hydroxide, ferimzone (TF164), fluazinam, fluobenzimine, fluquinconazole, fluorimide, flusilazole, flutolanill flutriafol, folpet, fosetyl aluminium, fuberidazole, fulsulfemide (MT-F651), furalaxyl, furconazole, furmecyclox, guazatine, hexaconazole, ICI ASS 04, imazalil, imiben-conazole, iprobenfos, iprodione, isoprothiolane, KNF 317, copper compounds, such as copper oxychloride, oxine-copper, copper oxide, mancozeb, maneb, mepanipyrim (KIF 3535), metconazole, mepronil, metalaxyl, methasulfocarb, methfuroxam, MON 24000, myclobutanil, nabam, nitrothalidopropyl, nuarimol, ofurace, oxadixyl, oxycarboxin, penconazole, pencycuron, PP 969, probenazole, propineb, prochloraz, procymidon, propamocarb, propiconazole, prothiocarb, pyracarbolid, pyrazophos, pyrifenox, pyroquilon, rabenzazole, RH7592, sulfur, tebuconazole, TF 167, thiabendazole, thicyofen, thiophanate-methyl, thiram, tolclofos-methyl, tolyfluanid, triadimefon, triadimenol, tricyclazole, tridemorph, triflumizol, triforine, validamycin, vinchlozolin, XRD 563, zineb, sodium dodecylsulfonate, sodium dodecyl sulfate, sodium C13/C15-alcohol ether sulfonate, sodium ceto-stearyl phosphate ester, sodium dioctylsulfosuccinate, sodium isopropylnaphthalenesulfonate, sodium methylenebisnaphthalenesulfonate, cetyltrimethylammonium chloride, salts of long-chain primary, secondary or tertiary amines, alkylpropyleneamines, lauryl-pyrimidinium bromide, ethoxylated quaternated fatty amines, alkyldimethylbenzylammonium chloride and 1-hydroxyethyl-2-alkylimidazolin.

The abovementioned components are known active substances, many of which are described in Ch. R Worthing, U. S. B. Walker, The Pesticide Manual, 7th Edition (1983), British Crop Protection Council.

Moreover, the active substance according to the invention, in its commercially available formulations and in the use forms prepared with these formulations, can exist in the form of a mixture with other active substances, such as insecticides, attractants, sterilants, acaricides, nematicides or herbicides. The insecticides include, for example, phosphoric esters, carbamates, carboxylic esters, formamidines, tin compounds, substances produced by microorganisms and the like. Preferred components in mixtures are:

1. From the group of the phosphorus compounds acephate, azamethiphos, azinphosethyl, azinphosmethyl, bromophos, bromophos-ethyl, chlorfenvinphos, chlormephos, chlorpyrifos, chlorpyrifos-methyl, demeton, demeton-S-methyl, demeton-S-methyl sulfone, dialifos, diazinon, dichlorvos, dicrotophos, 0,0-1,2,2,2-tetrachloroethylphosphorothioate (SD 208 304), dimethoate, disulfoton, EPN, ethion, ethoprophos, etrimfos, famphur, fenamiphos, fenitrothion, fensulfothion, fenthion, fonofos, formothion, heptenophos, isazophos, isothioate, isoxathion, malathion, methacrifos, methamidophos, methidathion, salithion, mevinphos, monocrotophos, naled, omethoate, oxydemeton-methyl, parathion, parathion-methyl, phenthoate, phorate, phosalone, phosfolan, phosmet, phosphamidon, phoxim, pirimiphos-ethyl, pirimiphos-methyl, profenofos, propaphos, proetamphos, prothiofos, pyraclofos, pyridapenthion, quinalphos, sulprofos, temephos, terbufos, tetrachlorvinphos, thiometon, triazophos, trichlorphon, vamidothion.

2. From the group of the carbamates aldicarb, 2-sec-butylphenylmethylcarbamate (BPMC), carbaryl, carbofuran, carbosulfan, cloethocarb, benfuracarb, ethiofencarb, furathiocarb, isoprocarb, methomyl, 5-methyl-m-cumenylbutyryl methylcarbamate, oxamyl, pirimicarb, propoxur, thiodicarb, thiofanox, ethyl 4,6,9-triaza-4-benzyl-6,10-dimethyl-8-oxa-7-oxo-5,11-dithia-9-dodecenoate (OK 135), 1-methylthio-(ethylideneamino)-N-methyl-N-(morpholinothio)carhamate (UC 51717).

3. From the group of the carboxylic esters allethrin, alphametrin, 5-benzyl-3-furylmethyl (E)-(IR)-cis-2,2-di-methyl-3-(2-oxothiolan-3-ylidenemethyl) cyclopropane-carboxylate, bioallethrine, bioallethrine( (S)cyclopentenyl isomer), bioresmethtin, biphenate, (RS)-1-cyano-1-(6-phenoxy-2-pyridyl)methyl (1RS)-trans-3-(4-tert-butylphenyl)-2,2-dimethylcyclopropanecarboxylate (NCI 85193), cycloprothrin, cyhalothrin, cypermethrin, cyphenothrin, deltamethrin, empenthrin, esfenvalerate, fenfluthrin, fenpropathrin, fenvalerate, flucythrinate, flumethrin, fluvalinate (D isomer), permethrin, pheothrin ((R) isomer), d-prallethrin, pyrethrins (natural products), resmethrin, tefluthrin, tetramethrin, tralomethrin.

4. From the group of the amidines amitraz, chlordimeform.

5. From the group of the tin compounds cyhexatin, fenbutatin oxide.

6. Others abamectin, Bacillus thuringiensis, bensultap, binapacryl, bromopropylate, buprofezin, camphechlor, cartap, chlorobenzilate, chlorfluazuron, 2-(4-(chlorophenyl)-4,5-diphenylthiophene (UBI-T 930), chlorfentezine, 2-naphthylmethyl cyclopropanecarboxylate (Ro12-0470), cyromazin, ethyl N-(3,5-dichloro-4-(1,1,2,3,3,3-hexafluoro-1-propyloxy) phenyl)carbamoyl)-2-chlorobenzocarboximidate, DDT, dicofol, N-(N-(3,5-dichloro-4-(1,1,2,2-tetrafluoroethoxy)phenylamino)carbonyl)-2,6-difluorobenzamide (XRD 473), diflubenzuron, N-(2,3-dihydro-3-methyl-1,3-thiazol-2-ylidene)-2,4-xylidine, dinobuton, dinocap, endosulfan, ethofenprox, (4-ethoxyphenyl)(dimethyl) (3-(3-phenoxyphenyl) propyl)silane, (4-ethoxyphenyl)(3-(4-fluoro-3-phenoxyphenyl)propyl)demethylsilane, fenoxycarb, 2-fluoro-5-(4-(4-ethoxyphenyl)-4-methyl-1-pentyl) diphenyl ether (MTI 800), granulosis and nuclear polyhedrosis viruses, fenthiocarb, flubenzimine, flucycloxuron, flufenoxuron, gamma-HCH, hexythiazox, hydramethylnon (AC 217300), ivermectin, 2-nitromethyl-4,5-dihydro-6H-thiazine (SD 52618), 2-nitromethyl-3,4-dihydrothiazole (SD 35651), 2-nitromethylene-1,2-thiazinan-3-ylcarbamaldehyde (WL 108477), propargite, teflubenzuron, tetradifon, tetrasul, thiocyclam, triflumuron.

The active substance content of the use forms prepared with the commercially available formulations can vary within wide limits; the active substance concentration of the use forms can be from 0.0001 up to 95% by weight of active substance, preferably between 0.001 and 1% by weight. They are used in a customary manner which suits the use forms.

The active substances are well tolerated by plants, their toxicity to warm-blooded species is favorable, and they are suitable for controlling animal pests, in particular insects, arachnids, helminths and molluscs, very particularly preferably for controlling insects and arachnids which occur in agriculture, in livestock production, in forests, in the protection of stored products and of materials, and in the hygiene sector. They are active against normally sensitive and resistant species and against all or individual development stages. The abovementioned pests include:

From the order of the Acarina, for example, *Acarus siro*, Agras spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp., Tetranychus spp., Eotetranychus spp., Oligonychus spp., Eutetranychus spp.

From the order of the Isopoda, for example, *Oniscus asellus, Armadillidiumvulgare* and *Porcellio scaber.*

From the order of the Diplopoda, for example, *Blaniulus guttulatus.*

From the order of the Chilopoda, for example, *Geophilus carpophagus* and Scutigera spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus*, Gryllotalpa spp.,

*Locusta migratoria migratorioides, Melanoplus differentialis* and *Schistocerca gregaria*.

From the order of the Isoptera, for example, Reticulitermes spp.

From the order of the Anoplura, for example, *Phylloxera vastatrix*, Pemphigus spp., *Pediculus humanus corpotis*, Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci*.

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne braesicae, Cryptomyzus ribis, Doralie fabae, Doralis pomi, Eriosoma lanigerum, Hyalopterue arundinis, Macrosiphum avenae*, Myzus spp., *Phorodon humuli, Rhopalosiphum padi*, Empoasca spp., *Euscelue bilobatus, Nephotettix cincticeps, Lecanium corni, Saissetia oleae, Laodelphax striatellus, Nilaparvata lugens, Aonidiella aurantii, Aspidiotus hederae*, Pseudococcus spp., Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp., *Bucculatrix thurberiella, Phyllocnistis citrella*, Agrotis spp., Euxoa spp., Feltia spp., *Earias insulana*, Hellothis spp., *Laphygma exigua, Mamestra brassicae, Panolis flammea, Prodenia litura*, Spodoptera spp., Trichoplusia ni, *Carpocapsa pomonella*, Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortfix viridana*.

From the order of the Coleoptera, for example, *Anobium punctatum, Rhizopertha dominica, Bruchidius obtectus, Acanthoscelides obtectus, Hylotrupes baJulus, Agelastica alni, Leptinotarsa decemlineata, Phaedon cochleariae*, Diabrotica spp., *Psylloides chrysocephala, Epilachna varivestis*, Atomaria spp., *Oryzaephilus surinamensis*, Anthonumus spp., Sitophilus spp., *Otiorrhynchus sulcatus, Cosmopolites sordidus, Ceuthorrhynchus assimilis, Hypera poetica*, Dermestes spp., Trogoderma spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon solstitialis* and *Costelytra zealandica*.

From the order of the Hymenoptera, for example, Diprion spp., Hoplocampa spp., Lasius spp., *Monomoriumpharaonis* and Vespa spp.

From the order of the Diptera, for example, Aedes spp., Anopheles spp., Culex spp., *Drosophila melanogaster*, Musca epp., Fannia spp., *Calliphora erythrocephala*, Lucilia spp., Chrysomyia spp., Cuterebra spp., Gastrophilus spp., Hypobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa*.

From the order of the Siphonaptera, for example, *Xenopsylla cheopis* and Ceratophyllus spp.

From the order of the Arachnida, for example, *Scorpio maurus* and *Latrodectus mactans*.

From the class of the Helminthes, for example, Trichostrongulus, Ostertagia, Cooperia, Chabertia, Strongyloides, Oesophagostomum, Hyostrongulus, Ancylostoma, Ascaris, Heterakis, and also Fasciola and plant-injurious nematodes, for example those of the genera Meloidogyne, Heterodera, Ditylenchus, Aphelenchoides, Radopholus, Globodera, Pratylenchus, Longidorus and Xiphinema.

From the class of the Gastropoda, for example, Deroceras spp., Arion spp., Lymnaea spp., Galba spp., Succinea spp., Biomphalaria spp., Bulinus spp., Oncomelania spp. From the class of the Bivalva, for example, Dreissena spp.

The invention also relates to insecticidal and acaricidal compositions which contain the compounds of the formula 1 besides suitable formulation auxiliaries.

In general, the compositions according to the invention contain 1 to 95% by weight of the active substance of the formula 1.

They can be formulated in various ways, depending on the prevailing biological and/or chemical-physical parameters. The following are therefore suitable as possible formulations: wettable powders (WP), emulsifiable concentrates (EC), aqueous solutions (SC), emulsions, sprayable solutions, oil- or water-based dispersions (SC), suspoemulsions (SC), dusts (DP), seed-dressing products, granules in the form of microgranules, spray granules, coated granules and adsorption granules, water-dispersible granules (WG), ULV formulations, microcapsules, waxes or baits.

These individual types of formulations are known in principle and are described, for example, in: Winnacker-Küchler, "Chemische Technologie [Chemical Technology]", Volume 7, C. Hauser Verlag Munich, 4th Edition 1986; van Falkenberg, "Pesticides Formulations", Marcel Dekker New York, 2nd Ed. 1972–73; K. Martens, "Spray Drying Handbook", 3rd Ed. 1979, G. Goodwin Ltd. London.

The formulation auxiliaries required, such as inert materials, surfactants, solvents and other additives are also known and are described, for example, in: Watkins, "Handbook of Insecticide Dust Diluents and Carriers", 2nd Ed., Darland Books, Caldwell N.J.; H.v. Olphen, "Introduction to Clay Colloid Chemistry", 2nd Ed., J. Wiley & Sons, New York; Marschen, "Solvents Guide", 2nd Ed., Interscience, New York 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., New York 1964; Schönfeldt, "Grenzfl achenaktive Äthylenoxidaddukte [Surface-Active Ethylene Oxide Adducts]", Wiss. Verlagsgesell., Stuttgart 1976; Winnacker-Küchler, "Chemische Technologie", Volume 7, C. Hauser Verlag Munich, 4th Edition, 1986.

Based on these formulations, it is also possible to prepare combinations with other pesticidally active substances, fertilizers and/or growth regulators, for example in the form of a readymix or a tank mix. Wettable powders are preparations which are uniformly dispersible in water and which, beside the active substance, also contain wetting agents, for example polyoxethylated alkylphenols, polyoxethylated fatty alcohols, alkylsulfonates or alkylphenolsulfonates and dispersants, for example sodium ligninsulfonate, sodium 2,2'-dinaphthylmethane-6,6'-disulfonate, sodium dibutylnaphthalenesulfonate or else sodium oleylmethyltaurinate, in addition to a diluent or inert substance. Emulsifiable concentrates are prepared by dissolving the active substance in an organic solvent, for example butanol, cyclohexanone, dimethylformamide, xylene or else higher-boiling aromatics or hydrocarbons with an addition of one or more emulsifiers. Examples of emulsifiers which can be used are the following: calcium alkylarylsulfonates, such as calcium dodecylbenzenesulfonate, or nonionic emulsifiers, such as fatty acid polyglycol esters, alkylaryl polyglycol ethers, fatty alcohol polylycol ethers, propylene oxide/ethylene oxide condensation products, alkyl polyethers, sorbitan fatty acid esters, polyoxyethylene sorbitan fatty acid esters or polyoxyethylene sorbitol esters.

Dusts are obtained by grinding the active substance with finely divided solid substances, for example talc, natural clays such as kaolin, bentonite, pyrophyllite, or diatomaceous earth. Granules can be produced either by spraying the active substance onto adsorptive, granulated inert material or by applying active substance concentrates to the surface of carriers, such as sand, kaolinites or granulated inert material, by means of binders, for example polyvinyl alcohol, sodium polyacrylate or else mineral oils. Suitable active substances can also be granulated in the manner which is customary for the production of fertilizer granules, if desired in the form of a mixture with fertilizers.

In wettable powders, the active substance concentration is, for example, approximately 10 to 90% by weight, the remainder to 100% by weight is composed of customary formulation components. In the case of emulsifiable concentrates, the active substance concentration can be approximately 5 to 80% by weight. Formulations in the form of dusts usually contain 5 to 20% by weight of active substance, sprayable solutions approximately 2 to 20% by weight. In the case of granules, the active substance content partly depends on whether the active compound is in liquid or solid form and on which granulation auxiliary, fillers and the like are being used.

Besides, the abovementioned formulations of active substances contain, if appropriate, the adhesives, wetting agents, dispersants, emulsifiers, penetrants, solvents, fillers or carriers which are customary in each case.

For use, the concentrates, which are commercially available, are, if appropriate, diluted in the customary manner, for example using water in the case of wettable powders, emulsifiable concentrates, dispersions and also in the case of some microgranules. Preparations in the form of dusts and granulated preparations and sprayable solutions are conventionally not diluted any further with other inert substances prior to use.

The application rate required varies with external conditions, such as, inter alia, temperature and humidity. It can vary within wide limits, for example between 0.001 and 10.0 kg/ha or more of active ingredient, but it is preferably between 0.005 and 5 kg/ha.

The active substances according to the invention can be present in their commercially available formulations and in the use forms prepared with these formulations in the form of mixtures with other active substances, such as insecticides, attractants, sterilants, acaricides, nematicides, fungicides, growth-regulating substances or herbicides.

The pesticides include, for example, phosphoric esters, carbamates, carboxylic esters, formamidines, tin compounds, substances produced by microorganisms and the like. The following are preferred components in the mixtures:

1. From the group of the phosphorus compounds acephate, azamethiphos, azinphosethyl, azinphos-methyl, bromophos, bromophos-ethyl, chlorfenvinphos, chlormephos, chlorpyrifos, chlorpyrifos-methyl, demeton, demeton-S-methyl, demeton-S-methyl sulfone, dialifos, diazinon, dichlorvos, dicrotophos, 0,0-1,2,2,2-tetrachloroethylphosphorothioate (SD 208 304), dimethoate, disulfoton, EPN, ethion, ethoprophos, etrimfos, famphur, fenamiphos, fenitrothion, fensulfothion, fenthion, fonofos, formothion, heptenophos, isazophos, isothioate, isoxathion, malathion, methacrifos, methamidophos, methidathion, salithion, mevinphos, monocrotophos, naled, omethoate, oxydemeton-methyl, parathion, parathion-methyl, phenthoate, phorate, phosalone, phosfolan, phosmet, phosphamidon, phoxim, pirimiphos-ethyl, pirimiphos-methyl, profenofos, propaphos, proetamphos, prothiofos, pyraclofos, pyridapenthion, quinalphos, sulprofos, temephos, terbufos, tetrachlorvinphos, thiometon, triazophos, trichlorphon, vamidothion.

2. From the group of the carbamates aldicarb, 2-sec-butylphenylmethylcarbamate (BPMC), carbaryl, carbofuran, carbosulfan, cloethocarb, benfuracarb, ethiofencarb, furathiocarb, isoprocarb, methomyl, 5-methyl-m-cumenylbutyryl methylcarbamate, oxamyl, pirimicarb, propoxur, thiodicarb, thiofanox, ethyl 4,6,9-triaza-4-benzyl-6,10-dimethyl-8-oxa-7-oxo-5,11-dithia-9-dodecenoate (OK 135), 1-methylthio-(ethylideneamino)-N-methyl-N-(morpholinothio)carbamate (UC 51717).

3. From the group of the carboxylic esters allethrin, alphametrin, 5-benzyl-3-furylmethyl (E)-(IR)-cis-2,2-di-methyl-3-(2-oxothiolan-3-ylidenemethyl) cyclopropane-carboxylate, bioallethrine, bioallethrine( (S)-cyclopentenylisomer), bioresmethrin, biphenate, (RS)-I-cyano-1-(6-phenoxy-2-pyridyl)methyl (1RS)-trans-3-(4-tert-butylphenyl)-2,2-dimethylcyclopropanecarboxylate (NCI 85193), cycloprothrin, cyhalothrin, cypermethrin, cyphenothrin, deltamethrin, empenthrin, esfenvalerate, fenfluthrin, fenpropathrin, fenvalerate, flucythrinate, flumethrin, fluvalinate (D isomer), permethrin, pheothrin ((R) isomer), d-prallethrin, pyrethrins (natural products), resmethrin, tefluthrin, tetramethrin, tralomethrin.

4. From the group of the amidines amitraz, chlordimeform.

5. From the group of the tin compounds cyhexatin, fenbutatin oxide.

6. Others abamectin, *Bacillus thuringiensis*, bensultap, binapacryl, bromopropylate, buprofezin, camphechlor, cartap, chlorobenzilate, chlorfluazuron, 2-(4-(chlorophenyl)-4,5-diphenylthiophene (UBI-T 930), chlorfentezine, 2-naphthylmethyl cyclopropanecarboxylate (Ro12-0470), cyromazin, ethyl N-(3,5-dichloro-4-( 1,1,2,3,3,3-hexafluoro-1-propyloxy) phenyl)carbamoyl)-2-chlorobenzocarboximidate, DDT, dicofol, N-(N-(3,5-dichloro-4-(1,1,2,2-tetrafluoroethoxy)phenylamino)carbonyl)2,6-difluorobenzamide (XRD 473), diflubenzuron, N-(2,3-dihydro-3-methyl-1,3-thiazol-2-ylidene)2,4-xylidine, dinobuton, dinocap, endosulfan, ethofenprox, (4-ethoxyphenyl)-(dimethyl) (3-(3-phenoxyphenyl) propyl)silane, (4-ethoxyphenyl)(3-(4-fluoro-3-phenoxyphenyl)propyl)dimethylsilane, fenoxycarb, 1-fluoro-5-(4-(4-ethoxyphenyl)-4-methyl-1-pentyl) diphenyl ether (MTI 800), granulosis and nuclear polyhedrosis viruses, fenthiocarb, flubenzimine, flucycloxuron, flufenoxuron, gamma-HCH, hexythiazox, hydramethylnon (AC 217300), ivermectin, 2-nitromethyl-4,5-dihydro-6H-thiazine (SD 52618), 2-nitromethyl-3,4-dihydrothiazole (SD 35651), 2-nitromethylene-1,2-thiazinan-3-ylcarbamaldehyde (WL 108477), propargite, teflubenzuron, tetradifon, tetrasul, thiocyclam, triflumuron.

The active substance content of the use forms prepared with the commercially available formulations can be from 0.00000001 up to 95% by weight of active substance, preferably between 0.00001 and 1% by weight.

They are used in a customary manner which suits the use forms.

The active substances according to the invention are also suitable for controlling endoparasites and ectoparasites in the field of veterinary medicine and the field of animal keeping.

In this case, the active substances according to the invention are administered in a known manner, such as by oral administration in the form of, for example, tablets, capsules, drinks, granules, by dermal administration in the form of, for example, dipping, spraying, pouring on and spotting on, and dusting, and by parenteral administration, for example in the form of an injection.

Accordingly, the novel compounds of the formula 1 according to the invention can be employed particularly advantageously in livestock breeding (for example cattle, sheep, pigs, and poultry such as chickens, geese and the like). In a preferred embodiment of the invention, the novel compounds, if appropriate in suitable formulations (cf. above) are administered orally to the animals, if appropriate together with the drinking water or the feed. Since they are excreted in an effective fashion in feces, this allows the development of insects in the feces of the animals to be prevented in a very simple manner. The dosages and formulations which are suitable in each case will depend, in particular, on the species and the development stage of the livestock and also on the severity of the infection, and they can easily be determined and chosen by the customary methods. The novel compounds can be employed for example in cattle at dosages of 0.01 to 1 mg/kg of body weight.

The examples which follow are intended to illustrate the invention without imposing any limitation thereon.

A. Chemical examples

EXAMPLE 1

4-O-Benzylhydroxylamino-3-methoxy-2-methoxymethylpyridine 13 g of 4-chloro-3-methoxy-2-methoxymethylpyridine, 50 g of phenol and 30 g of O-benzylhydroxylamine are heated for 4 hours at 115° to 120° C. under nitrogen. After the batch has cooled, it is poured into a solution of 32 g of NaOH in 200 ml of water. The product is extracted using methylene chloride. The residue which remains after the methylene chloride and the excess O-benzylhydroxylamine have been distilled off is purified by column chromatography on silica gel with ethyl acetate. 14 g=74%

$^1$H-HMR (100 MHz, CDCl$_3$)=8.2 (d, 1H), 7.4 (s, 5H), 7.0 (d, 2H), 4.9 (s, 2H), 4.5 (s, 2H), 3.7 (s, 3H), 3.4 (s, 3H) ppm.

EXAMPLE 2

4-[O-Benzyl-N-(4-cis-tert-butylcyclohexyl)hydroxylamino]-3-methoxy-2-methoxymethylpyridine A solution of 5.4 g of 4-O-benzylhydroxylamino-3-methoxy-2-methoxymethylpyridine in 10 ml of absolute tetrahydrofuran is added dropwise under nitrogen to 2.8 g of potassium tert-butylate in 10 ml of absolute DMSO. A solution of 8.2 g of 4-trans-tert-butyl-O-tosylcyclohexanol in 15 ml of absolute THF is subsequently added dropwise, and the mixture is stirred for 14 hours at 50° C. The THF is then distilled off in vacuo and the residue is worked up with water and methylene chloride. The methylene chloride phase is purified over silica gel.

Yield: 3.5 g=43%.

$^1$H-NMR (100 MHz, CDCl$_3$)=8.3 (d, 1H), 7.3 (d, 1H), 7.3 (s, 5H), 4.7 (s, 2H), 4.6 (s, 2H), 3.9 (s, 3H), 3.7 (m, 1H), 3.5 (s, 3H), 0.9 to 2.1 (m, 9H), 0.8 (s, 9H) ppm.

EXAMPLE 3

4-[O-Benzyl-N-(4-cis-(1,1,3,3-tetramethylbutyl)cyclohexyl]hydroxylamino-3-methoxy-2-methoxymethylpyridine was synthesized analogously to Example 2 using 4-O-benzylhydroxylamino-3-methoxy-2-methoxymethylpyridine and trans-4-(1,1,3,3-tetramethylbutyl)-O-tosylcyclohexanol.

Yield: 26%.

$^1$H-NMR (100 MHz, CDCl$_3$)=8.3 (d, 1H), 7.4 (d, 1H), 7.3 (s, 5H) 4.7 (s, 2H), 4.6 (s, 2H) 3.9 (s, 3H), 3.7 (m, 1H), 3.5 (s, 3H), 1.4 to 2.1 (m, 9H), 0.9 and 1.0 (2s, 15H) ppm.

EXAMPLE 4

4-[O-Benzyl-N-(4-cis-tert-amylcyclohexyl)]hydroxylamino-3-methoxy-2-methoxy-methylpyridine hydrochloride was synthesized analogously to Example 2 using 4-O-benzylhydroxylamino-3-methoxy-2-methoxymethylpyridine and trans-4-tert-amyl-O-tosylcyclohexane.

Yield: 35%.

$^1$H-NMR (100 MHz, CDCl$_3$)=8.3 (t, 1H), 7.6 (d, 1H), 7.4 (s, 5H), 5.4 (m, 1H), 4.8 (s, 4H), 4.4 (m, 1H), 3.8 (s, 3H), 3.6 (s, 3H), 1.0 to 2.1 (m, 9H), 0.8 (s, t, 9H) ppm.

EXAMPLE 5

4-[4-cis-(1,1,3,3-Tetramethylbutyl)cyclohexylamino]-3-methoxy-2-methoxymethylpyridine hydrochloride 1.2 g of 4-[O-benzyl-N-(4-cis-(1,1,3,3-tetramethylbutyl))cyclohexyl]-hydroxylamino-3-methoxy-2-methoxymethylpyridine in 20 ml of methanol are hydrogenated with 0.5 g of Raney Nickel at atmospheric pressure until the uptake of hydrogen has ceased. The filtered solution is concentrated in vacuo and the residue is dissolved in hexane. When HCl in ether is added, the hydrochloride precipitates. It is filtered off with suction, washed with ether and dried. 0.8 g=85%

$^1$H-NMR (100 MHz, CDCl$_3$)=8.1 (t, 1H), 6.7 (d, 1H), 5.9 (m, 1H), 4.9 (s, 2H), 3.9 (s, 3H), 3.9 (m, 1H), 3.6 (s, 3H), 1.0 to 2.1 (m, 9H), 1.0 (2s, 15H) ppm.

EXAMPLE 6

4-(4-cis-tert-butylcyclohexylamino)-3-methoxy-2-methoxy-methylpyridine was prepared analogously to Example 5 using 4-[O-benzyl-N-(4-cis-tert-butylcyclohexyl)hydroxylamino]-3-methoxy-2-methoxy-methylpyridine (Example 2)

Yield: 90%

$^1$H-NMR (100 MHz, CDCl$_3$)=8.2 (t, 1H), 6.8 (d, 1H), 5.9 (m, 1H), 4.8 (s, 2H), 3.9 (s, 3H), 3.9 (m, 1H), 3.6 (s, 3H), 1.0 to 2.1 (m, 9H), 0.9 (s, 9H) ppm.

EXAMPLE 7

4-[4-cis-(1,1-Dimethylprop-1-yl)-cyclohexylamino]-3-methoxy-2-methoxymethylpyridine was prepared analogously to Example 5 using 4-[O-benzyl-N-(4-cis-tert-amylcyclohexyl)]hydroxylamino-3-methoxy-2-methoxymethylpyridine (Example 4).

The free base was liberated from the solution of the hydrochloride in methylene chloride by shaking with sodium hydrogencarbonate solution.

$^1$H-NMR (100 MHz, CDCl$_3$)=8.0 (d, 1H), 6.5 (d, 1H), 5.8 (d, 1H), 4.5 (s, 2H), 3.8 (s, 3H), 3.7 (m, 1H), 3.5 (s, 3H), 1.1 to 2.1 (m, 9H), 0.8 (s, t, 9H) ppm.

EXAMPLE 8

Ethyl 2,6-dimethyl-4-(cis-4-tert-butylcyclohexylamino) nicotinate 2.1 g of ethyl 4-chloro-2,6-dimethylnicotinate and 4.7 g of 4-cis-tert-butylcyclohexylamine are heated for 3 hours at 170° to 180° C. under nitrogen. After the syrupy mixture has cooled, it is extracted by shaking with water and methylene chloride, the organic phase is dried over CaCl$_2$, and the product is isolated by column chromatography (silica gel/ toluene: ethyl acetate 3:1).

Yield: 1.8 g $^1$H-NMR (100 MHz, CDCl$_3$)=0.85 (s, 9H), 1.37 (t, 3H), 2.37 and 2.60 (2s, 6H), 3.70 (m, 1H), 4.33 (q, 2H) ppm.

EXAMPLE 9

Ethyl 2-methyl-4-(cis-4-tert-amylcyclohexylamino) nicotinate 2.0 g of 4-chloro-2-methyl-3-ethoxycarbonylpyridine, 1.7 g of cis-4-tert-amylcyclohexane and catalytic amounts of ammonium chloride are heated for 10 hours at 100° C. After cooling, the mixture is taken up in 20 ml of methanol and neutralized using 2N sodium hydroxide solution. The resulting reaction mixture is dried in vacuo and the free base is extracted using dichloromethane. After drying with Na$_2$SO$_4$, filtration and removal of the solvent, 3.0 g of syrup remain.

$^1$H-NMR (100 MHz, CDCl$_3$)=8.2 (d, 1H), 7.2 (d, 1H), 4.4 (q, 2H), 3.6 (m, 1H), 1.4 (t, 3H) ppm.

EXAMPLE 10

Ethyl 2-methyl-4-(cis-4-phenylcyclohexylamino) nicotinate

The synthesis was carried out analogously to Example 9, using 4-chloro-2-methyl-3-ethoxycarbonylpyridine and 4-cis-phenylcyclohexylamine, m.p.: 191° C.

EXAMPLE 11

2-methoxymethyl-3-methoxy-4-(4-cis-tert-butylcoyclohexyloxy)pyridine

A mixture of 1.88 g (10 mmol) of 2-methoxymethyl-3-methoxy-4-chloropyridine, 2.03 g (13 mmol) of 4-cis-tert-butylcyclohexanol and 15 ml of DMSO is added dropwise to 0.36 g (12 mmol) of NaH (80% pure) in 25 ml of DMSO at 25° C. The mixture is subsequently stirred for 6 hours at 60° C. For working up, saturated ammonium chloride solution is added at 20° to 25° C. and the mixture is extracted using ethyl acetate. The reaction product is purified by chromatography (SiO$_2$; first EtOAc/CH$_2$Cl$_2$ [1:3] then EtOAc).

Yield: 1.23 g (40%)

$^1$H-NMR (CDCl$_3$)=8.2 (d, 1H), 6.8 (d, 1H), 4.6 (s, 2H), 4.2 (m, 1H), 3.8 (s, 3H), 3.5 (s, 1H), 0.9–2.3 (m, 9H), 0.9 (s, 9H).

EXAMPLE 12

Ethyl 2,6-dimethyl-4-[2-(2,4-dimethylphenoxy) ethylamino]nicotinate was synthesized analogously to Example 8 using ethyl 4-chloro-2,6-dimethylnicotinate and 2-(2,4-dimethylphenoxy)ethylamine.

EXAMPLE 13

Ethyl 2,6-dimethyl-4-(2,2,6,6-tetramethylpiperidin-4-ylamino)nicotinate was synthesized analogously to Example 8 using ethyl 4-chloro-2,6-dimethylnicotinate and 2,2,6,6-tetramethyl-4-aminopiperidine. M.p.: 89° to 90° C.

EXAMPLE 14

Ethyl 2,6-dimethyl-4-[2-methyl-3-(4-tert-butylcyclohexyl)propylamino]nicotinate was synthesized analogously to Example 8 using ethyl 4-chloro-2,6-dimethylnicotinate and 2-methyl-3-(4-tert-butylcyclohexyl)propylamine n$_D^{23}$:1.4738.

EXAMPLE 15

Ethyl 2,6-dimethyl-4-(dec(2)ylamino)nicotinate was synthesized analogously to Example 8 using ethyl 4-chloro-2,6-dimethylnicotinate and 2-aminodecane. n$_D^{23}$:1.4700.

EXAMPLE 16

Ethyl 2,6-dimethyl-4-(4-phenylcyclohexylamino) nicotinate was prepared analogously to Example 8 using ethyl 4-chloro-2,6-dimethylnicotinate and 4-phenylcyclohexylamine. n$_D^{23}$:1.5389.

EXAMPLE 17

Ethyl 2,6-dimethyl-4-[N-(4-butylphenyl)piperidin(4)-ylamino]-nicotinate was prepared analogously to Example 8 using ethyl 4-chloro-2,6-dimethylnicotinate and 4-amino-N-(4-butylphenyl)piperidine. n$_D^{23}$:1.5400.

EXAMPLE 18

2-Acetoxymethyl-3-methoxy-4-(4-cis-tert-butylcyclohexyloxy)piperidine 7.45 g (23.75 mmol) of m-chloroperbenzoic acid (55% pure) are added at 25° C. to 4.16 g (15 mmol) of 2-methyl-3-methoxy-4-(4-cis-tert-butylcyclohexyloxy)pyridine in 100 ml of CH$_2$Cl$_2$, and the mixture is stirred at this temperature for 28 hours. After washing with saturated NaHCO$_3$ solution, evaporation of the solvent and purification by chromatography [SiO$_2$;EtOAc/AcOH (5:1)], 4.19 g (95.2%) of 2-methyl-3-methoxy-4-(4-cis-tert-butylcyclohexyloxy) pyridine N-oxide are obtained, and this product and 20 ml of acetic anhydride are heated for 1 hour at 120° C. The reaction mixture is evaporated in vacuo and the residue is purified by chromatography (SiO$_2$;EtOAc).

Yield: 4.95 g (99%)

$^1$H-NMR (CDCl$_3$)=8.2 (d, 1H), 6.8 (d, 1H), 5.2 (s, 2H), 4.6 (m, 1H), 3.9 (s, 3H), 2.1 (s, 3H), 0.9 to 2.3 (m, 9H), 0.9 (s, 9H), ppm.

EXAMPLE 19

4-O-Benzylhydroxylamino-3-ethoxy-2-ethoxymethylpyridine

The synthesis was carried out analogously to Example 1 using 4-chloro-3-ethoxy-2-ethoxymethylpyridine and O-benzylhydroxylamine.

Yield: 90%

$^1$H-NMR (100 MHz, CDCl$_3$): 8.2 (d, 1H), 7.5 (s, 1H), 7.4 (s, 5H), 7.0 (d, 1H), 4.9 (s, 2H), 4.6 (s, 2H), 3.9 (q, 2H), 3.6 (9.2H), 1.3 (t, 3H), 1.2 (t, 3H) ppm.

EXAMPLE 20

4-O-Benzylhydroxylamino-3-bromo-2-methoxymethylpyridine

The synthesis was carried out analogously to Example 1 using 4-chloro-3-bromo-2-methoxymethylpyridine and O-benzylhydroxylamine.

Yield: 95%

$^1$H-NMR (100 MHz, CDCl$_3$): δ: 8.3 (d, 1H), 7.7 (s, 1H), 7.4 (m, 1H), 6.9 (d, 1H), 4.9 (s, 2H), 4.6 (s, 2H), 3.5 (s, 3H) ppm.

EXAMPLE 21

4-O-Benzylhydroxylamino-3-methoxy-2-allyloxypyridine

The synthesis was carried out analogously to Example 1 using 4-chloro-3-methoxy-2-allyloxypyridine and O-benzylhydroxylamine.

Yield: 46.9%

$^1$H-NMR (100 MHz, CDCl$_3$): δ: 8.2 (d, 1H), 7.5 (s, 1H), 7.4 (s, 5H), 5.8–6.1 (m, 1H), 5.1–5.4 (m, 2H), 4.9 (s, 2H), 4.1–4.2 (m, 2H), 3.8 (s, 3H) ppm.

EXAMPLE 22

4-O-Benzylhydroxylamino-3-chloro-2-methoxymethylpyridine

The synthesis was carried out analogously to Example 1 using 3,4-dichloro-2-methoxymethylpyridine and O-benzylhydroxylamine.

Yield: 52.8%

$^1$H-NMR (100 MHz, CDCl$_3$): δ: 8.3 (d, 1H), 7.6 (s, 1H), 7.3–7.5 (m, 5H), 7.0 (s, 1H), 4.9 (s, 2H), 4.6 (s, 2H), 3.5 (s, 3H) ppm.

EXAMPLE 23

4-[O-Benzyl-N-(4-cis-phenylcyclohexyl)hydroxylamino]-3-methoxy-2-methoxymethylpyridine was prepared analogously to Example 2 using 4-O-benzylhydroxylamino-3-methoxy-2-methoxymethylpyridine (Example 1) and trans-4-phenyl-1-tosyloxycyclohexane.

Yield: 39%

$^1$H-NMR (100 MHz, CDCl$_3$): δ: 8.2 (d, 1H), 7.3 (m, 6H), 4.7 (s, 2H), 4.6 (s, 2H), 3.9 (s, 3H), 3.8 (m, 1H), 3.5 (s, 3H), 2.8 (m, 1H), 1.5–2.4 (m, 8H) ppm.

EXAMPLE 24

4-[O-Benzyl-N-(4-cis-(4-ethoxyphenyl)cyclohexyl)hydroxylamino]-3-methoxy-2-methoxymethypyridine was prepared analogously to Example 2 using 4-O-benzylhydroxylamino-3-methoxy-2-methoxymethylpyridine (Example 1) and trans-4-(4-ethoxyphenyl)-1-tosyloxycyclohexane.

Yield: 46%

$^1$H-NMR (CDCl$_3$, 100 MHz): δ: 8.2 (d, 1H), 7.3 (m, 6H), 7.0 (m, 4H), 4.7 (s, 2H), 4.6 (s, 2H), 4.0 (q, 2H), 3.9 (s, 3H), 3.8 (m, 1H), 3.5 (s, 3H), 2.8 (m, 1H), 1.4 (t, 3H), 1.4–2.3 (m, 8H) ppm.

EXAMPLE 25

4-(O-Benzyl-N-decyl-hydroxylamino)-3-methoxy-2-methoxymethylpyridine was prepared analogously to Example 2 using 4-O-benzylhydroxylamino-3-methoxy-2-methylpyridine (Example 1) and dodecyl bromide.

Yield: 80%

$^1$H-NMR (100 MHz, CDCl$_3$): δ: 8.2 (d, 1H), 7.3 (s, 5H), 7.3 (d, 1H), 4.7 (s, 2H), 4.6 (s, 2H), 3.8 (s, 3H), 3.5 (s, 3H), 3.3 (t, 2H), 1.1–1.8 (m, 16H), 0.9 (t, 3H) ppm.

EXAMPLE 26

4-(4-cis-Phenylcyclohexylamino)-3-methoxy-2-methoxymethylpyridine was prepared analogously to Example 5 using 4-[O-benzyl-N-(4-cis-phenylcyclohexyl)hydroxylamino]-3-methoxy-2-methoxymethylpyridine (Example 23)

Yield: 100%

$^1$H-NMR (100 MHz, CDCl$_3$): δ: 8.1 (d, 1H), 7.2 (m, 5H), 6.5 (d, 1H), 4.9 (d, 1H), 4.5 (s, 2H), 4.9 (s, 3H), 4.8 (m, 1H), 3.5 (s, 3H), 2 (m, 1H), 1.6–2.2 (m, 9H) ppm.

EXAMPLE 27

4-[4-cis-(4-ethoxyphenyl)cyclohexylamino)-3-methoxy-2-methoxymethylpyridine was prepared analogously to Example 5 using 4-[O-benzyl-N-(4-cis-(4-ethoxyphenyl)cyclohexyl)hydroxylamino]-3-methoxy-2-methoxymethylpyridine (Example 24).

Yield: 74%

$^1$H-NMR (100 MHz, CDCl$_3$): δ: 8.1 (d, 1H), 6.9 (m, 4H), 6.5 (d, 1H), 4.9 (d, 1H), 4.6 (s, 2H), 4.0 (q, 2H), 3.9 (s, 3H), 3.8 (m, 1H), 2.5 (m, 1H), 1.6–2.1 (m, 8H), 1.4 (t, 3H) ppm.

EXAMPLE 28

4-Decylamino-3-methoxy-2-methoxymethylpyridine was prepared analogously to Example 5 using 4-(O-benzyl-N-decylhydroxylamino)-3-methoxy-2-methoxymethylpyridine (Example 25).

Yield: 84%

$^1$H-NMR (100 MHz, CDCl$_3$): δ: 8.0 (d, 1H), 6.4 (d, 1H), 4.6 (t, 1H), 4.5 (s, 2H), 3.0 (s, 3H), 2.0 (s, 3H), 3.1 (q, 2H), 1.2–1.6 (m, 16H), 0.9 (t, 3H) ppm.

EXAMPLE 29

4-[O-Benzyl-N-(1,4-dioxaspiro[4.5]dec-8-yl)hydroxylamino]-3-methoxy-2-methoxymethylpyridine

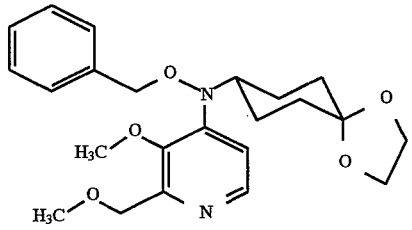

The synthesis was carried out analogously to Example 2 using 4-O-benzylhydroxylamino-3-methoxy-2-methoxymethylpyridine (Example 1) and 8-tosyloxy-1,4-dioxaspiro[4,5]decane.

Yield: 78%

$^1$H-NMR (100 MHz, CDCl$_3$): 8.2 (d, 1H), 7.4 (s, 5H), 7.3 (d, 1H), 4.7 (s, 2H), 4.6 (s, 2H), 3.9 (s, 3H), 3.8 (s, 3H), 3.7 (m, 1H), 3.5 (s, 4H), 1.4–2.3 (m, 8H) ppm.

EXAMPLE 30

4-[O-Benzyl-N-(3,3-dimethyl-1,5-dioxaspiro[5.5]undecan(9)yl)hydroxylamino]-3-methoxy-2-methoxymethylpyridine

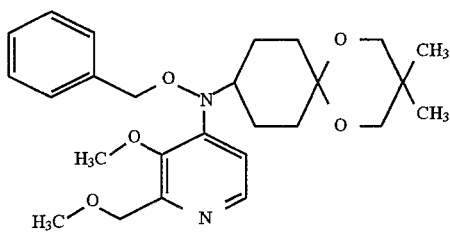
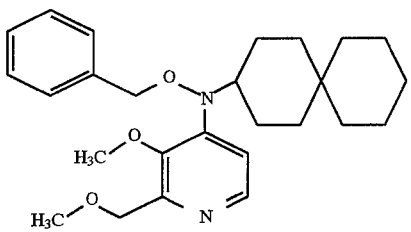

was prepared analogously to Example 2 using 4-O-benzylhydroxylamino-3-methoxy-2-methoxymethylpyridine (Example 1) and 3,3-dimethyl-9-tosyloxy-1,5-dioxaspiro[5,5]undecane.
Yield: 68%
¹H-NMR (100 MHz, CDCl₃): δ: 8.2 (d, 1H), 7.3 (m, 5H), 7.2 (d, 1H), 4.7 (s, 2H), 4.6 (s, 2H), 9.8 (s, 3H), 3.7 (m, 1H), 3.5 (m, 7H), 1.2–2.4 (m, 12H), 1.0 (s, 6H) ppm.

was prepared analogously to Example 2 using 4-O-benzylhydroxylamino-3-methoxy-2-methoxymethylpyridine (Example 1) and 3-tosyloxyspiro[5,5]undecane.
Yield: 81%
¹H-NMR (CDCl₃, 100 MHz): δ8.2 (d, 1H), 7.4 (m, 5H), 7.2 (d, 1H), 4.6 (s, 2H), 4.7 (s, 2H), 3.8 (s, 3H), 3.7 (m, 1H) 3.5 (s, 3H), 1.0–2.0 (m, 18H) ppm.

EXAMPLE 31

4-[O-Benzyl-N-(4-cis-tert-butylcyclohexyl)hydroxylamino]-3-bromo-2-methoxymethylpyridine was prepared analogously to Example 2 using 4-O-benzylhydroxylamino-3-bromo-2-methoxymethylpyridine (Example 20) and 4-trans-tert-butyl-1-tosyloxycyclohexane.
Yield: 56.4%
¹H-NMR (100 MHz, CDCl₃): δ: 8.4 (s, 1H), 7.2–7.4 (m, 6H), 4.6 (s, 2H), 4.7 (s, 2H), 3.5 (s, 3H), 3.5 (m, 1H), 1.0–2.0 (m, 9H), 0.8 (s, 9H)

EXAMPLE 32

4-[O-Benzyl-N-(4-cis-phenylcyclohexyl)hydroxylamino]-3-bromo-2-methoxymethylpyridine was prepared analogously to Example 2 using 4-O-benzylhydroxylamino-3-bromo-2-methoxymethylpyridine (Example 20) and trans-4-phenyl-1-tosyloxycyclohexane.
Yield: 29.9%
¹H-NMR (100 MHz, CDCl₃): δ: 8.4 (d, 1H), 7.2–7.4 (m, 11H), 4.7 (s, 2H), 4.6 (s, 2H), 3.5 (s, 3H), 3.6 (m, 1H), 2.9 (m, 1H), 1.3–2.3 (m, 8H) ppm.

EXAMPLE 33

4-[O-benzyl-N-(spiro[5,5]undecan(3)yl)hydroxyamino]-3-methoxy-2-methoxymethylpyridine

EXAMPLE 34

4-[O-Benzyl-N-(spiro[5,5]undecan(3)yl)hydroxylamino]-3-chloro-2-methoxymethylpyridine

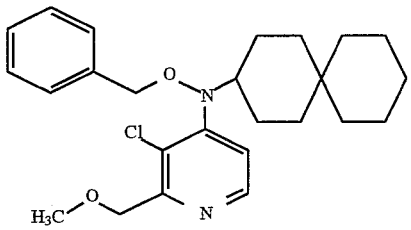

was prepared analogously to Example 2 using 4-O-benzylhydroxylamino-3-chloro-2-methoxymethylpyridine (Example 22) and 3-tosyloxyspiro[5,5]undecane.
Yield: 77%
¹H-NMR (CDCl₃, 100 MHz): δ: 8.3 (d, 1H), 7.3 (m, 5H), 7.3 (d, 1H), 4.6 (s, 2H), 4.7 (s, 2H), 4.6 (s, 2H), 3.5 (s, 3H), 3.3 (m, 1H), 0.9–2.0 (m, 18H) ppm.

EXAMPLE 35

4-[O-Benzyl-N-(4-cis(4(2(2,5,5-trimethyl-1,5-dioxan-2-yl) ethoxy)phenyl)cyclohexyl)hydroxylamino]-3-methoxy-2-methoxymethylpyridine

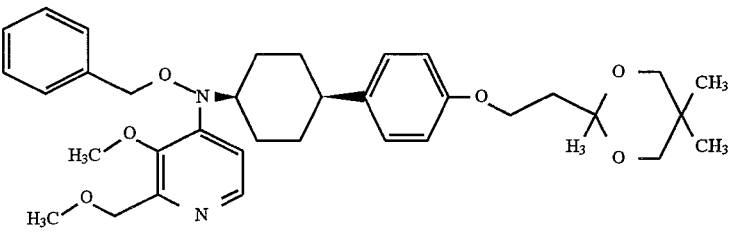

was prepared analogously to Example 2 using 4-O-benzylhydroxylamino-3-methoxy-2- methoxymethylpyridine (Example 1) and trans-4-(4-(2-(2,5,5-trimethyl-1,5-dioxan-2-yl)ethoxy)phenyl)-1-tosyloxycyclohexane.

Yield: 34%

$^1$H-NMR (100 MHz, CDCl$_3$): δ: 8.2 (d, 1H), 7.1–7.4 (m, 9H), 6.8 (d, 1H), 4.7 (s, 2H), 4.6 (s, 2H), 4.2–4.1 (m, 4H), 3.9 (m, 1H), 3.9 (s, 3H), 3.5 (q, 4H), 3.5 (s, 3H), 2.8 (m, 1H), 1.5–2.4 (m, 4H), 1.5 (s, 3H), 1.0 (s, 3H), 0.9 (s, 3H) ppm.

EXAMPLE 36

4-[O-Benzyl-N-4-cis<-(4-tetrahydrofur(2)ylmethoxy)phenyl>-cyclohexylamino]-3-methoxy-2-methoxymethylpyridine was prepared analogously to Example 2 using 4-O-benzylhydroxylamino-3-methoxy-2-methoxymethylpyridine (Example 1) and trans-4-<4-(tetrahydrofur(2)ylmethoxy)phenyl-1-tosyloxycyclohexane.

Yield: 51.4%

$^1$H-NMR (100 MHz, CDCl$_3$): δ: 8.2 (d, 1H), 7.2–7.4 (m, 9H), 6.8 (d, 1H), 4.6 (s, 2H), 4.7 (s, 2H), 4.3 (m, 1H), 3.9 (s, 1H) 3.8–4.1 (m, 5H), 3.5 (s, 3H), 2.8 (m, 1H), 1.5–2.2 (m, 12H).

EXAMPLE 37

4-[O-Benzyl-N-(4-cis-(4-(dimethyl-tert-butylsilyloxy)phenyl)cyclohexyl)hydroxylamino-3-methoxy-2-methoxymethylpyridine was prepared analogously to Example 2 using 4-O-benzylhydroxylamino-3-methoxy-2-methoxymethylpyridine (Example 1) and trans-4-(4-(dimethyl-tert-butylsilyloxy)phenyl)-1-tosyloxycyclohexane.

Yield: 23%

$^1$H-NMR (100 MHz, CDCl$_3$): δ: 8.2 (d, 1H), 7.1–7.4 (m, 9H), ... 8 (d, 1H), 4.7 (s, 2H), 4.6 (s, 2H), 3.9 (s, 3H), 3.9 (m, 1H), 3.4 (s, 3H), 2.8 (m, 1H), 1.5–2.2 (m, 8H), 1.0 (s, 9H), 0.2 (s, 6H) ppm.

EXAMPLE 38

4-[O-Benzyl-N-(4-cis-(4-(2,2-dimethoxyethoxy)phenyl)cyclohexyl)hydroxylamino]3-methoxy-2-methoxymethylpyridine was prepared analogously to Example 2 using 4-O-benzylhydroxylamino-3-methoxy-2-methoxymethylpyridine (Example 1) and trans-4-(4-(2,2-dimethoxyethoxy)phenyl)-1-tosyloxycyclohexane.

Yield: 66.2%

$^1$H-NMR (100 MHz, CDCl$_3$): δ: 8.2 (d, 1H), 7.2 (m, 9H),7.2–7.4 (m, 9H), 6.8 (d, 1H), 5.3 (s, 1H), 4.8 (t, 1H), 4.7 (s, 2H), 4.6 (s, 2H), 4.0 (d, 2H), 3.9 (m, 1H), 3.9 (s, 3H), 3.5 (s, 3H), 3.4 (s, 6H), 2.8 (m, 1H), 1.5–2.1 (m, 8H) ppm.

EXAMPLE 39

4-[O-Benzyl-N-(4-cis-(4-but-2-oxy-phenyl)cyclohexyl)hydroxylamino]-3-methoxy-2-methoxymethylpyridine was prepared analogously to Example 2 using 4-O-benzylhydroxylamino-3-methoxy-2-methoxymethylpyridine (Example 1) and trans-4-(4-but-2-oxy-phenyl)-1-tosyloxycyclohexane Yield: 49.0%

$^1$H-NMR (100 MHz, CDCl$_3$): δ: 8.2 (d, 1H), 7.1–7.4 (m, 9H), 6.8 (d, 2H), 4.7 (s, 2H), 4.6 (s, 2H), 4.3 (m, 1H), 3.9 (s, 3H), 3.8 (m, 1H), 3.5 (s, 3H), 2.8 (m, 1H), 1.5–2.3 (m, 10H), 1.3 (d, 3H), 1.0 (t, 3H) ppm.

EXAMPLE 40

4-[O-Benzyl-N-(4-cis-4-(2-ethoxyethoxy)phenyl)cyclohexyl)hydroxylamino]-3-methoxy-2-methoxymethylpyridine was prepared analogously to Example 2 using 4-O-benzylhydroxylamino-3-methoxy-2-methoxymethylpyridine (Example 1) and trans-4-[4-(2-ethoxyethoxy)phenyl]-1-tosyloxycyclohexane.

Yield: 56.4%

$^1$H-NMR (100 MHz, CDCl$_3$): δ: 8.2 (d, 1H), 7.2–7.4 (m, 9H), 6.8 (d, 1H), 4.6 (s, 2H), 4.7 (s, 2H), 4.2 (t, 2H), 3.9 (s, 3H), 3.9 (m, 1H), 3.8 (t, 2H), 3.6 (q, 2H), 3.5 (s, 3H), 2.8 (m, 1H), 1.5–2.2 (m, 8H), 1.2 (t, 3H) ppm.

EXAMPLE 41

O-Benzyl-N-(4-cis-{4-[2-(methoxy-ethoxy)-ethoxy]-phenyl}cyclohexyl)-N-(3-methyl-2-methoxymethyl-pyridine-4-yl)-hydroxylan was prepared analogously to Example 2 using 4-O-benzylhydroxylamino-3-methoxy-2-methoxymethylpyridine (Example 1) and trans-4-[4-(2-(2-methoxyethoxy)ethoxy)phenyl]-1-tosyloxycyclohexane.

Yield: 42.4%

$^1$H-NMR (100 MHz, CDCl$_3$): δ: 8.2 (d, 1H), 7.2 (m, 9H), 6.8 (d, 1H), 4.7 (s, 2H), 4.6 (s, 2H), 4.1 (m, 2H), 3.9 (m, 2H), 3.9 (s, 3H), 3.9–3.8 (m, 1H), 3.8 (m, 2H), 3.6 (m, 2H), 3.5 (s, 3H), 3.4 (s, 3H), 2.8 (m, 1H), 1.5–2.2 (m, 8H) ppm.

EXAMPLE 42

4-[O-Benzyl-N-(4-cis-(4-propoxyphenyl)cyclohexyl)hydroxylamino]-3-methoxy-2-methoxymethylpyridine was prepared analogously to Example 2 using 4-O-benzylhydroxylamino-3-methoxy-2-methoxymethylpyridine (Example 1) and trans-4-(propoxyphenyl)-1-tosyloxycyclohexane.

Yield: 50.3%

$^1$H-NMR (100 MHz, CDCl$_3$): δ: 8.2 (d, 1H), 7.1–7.4 (m, 9H), 6.8 (d, 1H), 4.7 (s, 2H), 4.6 (s, 2H), 3.9 (t, 2H), 3.9 (s, 3H), 3.8 (m, 1H), 3.5 (s, 3H), 2.8 (m, 1H), 1.5–2.3 (m, 10H), 1.1 (t, 3H) ppm.

EXAMPLE 43

4-[O-benzyl-N-(4-cis-(4-isopropoxyphenyl)cyclohexyl)hydroxylamino]-3-methoxy-2-methoxymethylpyridine was prepared analogously to Example 2 using 4-O-benzylhydroxylamino-3-methoxy-2-methoxymethylpyridine (Example 1) and trans-4-(4-isopropoxyphenyl)-1-tosyloxycyclohexane.

Yield: 54.6%

$^1$H-NMR (100 MHz, CDCl$_3$): δ: 8.2 (d, 1H), 7.1–7.4 (m, 9H), 6.8 (d, 1H), 4.7 (s, 2H), 4.6 (s, 2H), 4.5 (m, 1H), 3.9 (s, 3H), 3.5 (s, 3H), 2.8 (m, 1H), 1.5–2.2 (m, 8H), 1.3–1.4 (d, 6H) ppm.

EXAMPLE 44

4-[O-Benzyl-N(4-cis-(4-butoxyphenyl)cyclohexyl)hydroxylamino]-3-methoxy-2-methoxymethylpyridine was prepared analogously to Example 2 using 4-O-benzylhydroxylamino-3-methoxy-2-methoxymethylpyridin (Example 1) and trans-4-(4-butoxyphenyl)-1-tosyloxycyclohexane.

Yield: 55.6%

$^1$H-NMR (100 MHz, CDCl$_3$): δ: 8.2 (d, 1H), 7.2–7.4 (m, 9H), 6.8 (d, 1H), 4.6 (s, 2H), 4.7 (s, 2H), 3.9 (m, 2H), 3.8 (s,

3H), 3.9 (m, 1H), 3.5 (s, 3H), 2.8 (m, 1H), 1.5–2.3 (m, 12H), 1.0 (t, 3H) ppm.

EXAMPLE 45

4-[O-Benzyl-N-(4-cis-tert-amylcyclohexyl) hydroxylamino]-3-bromo-2-methoxymethylpyridine was prepared analogously to Example 2 using 4-O-benzylhydroxylamino-3-bromo-2-methoxymethylpyridine (Example 20) and trans-4-(1,1,3,3-tetramethylbutyl)-1-tosyloxycyclohexane.

Yield: 31%

$^1$H-NMR (100 MHz, CDCl$_3$): δ: 8.5 (d, 1H), 7.4 (q, 1H), 7.3 (m, 5H), 4.7 (s, 2H), 4.6 (s, 2H), 3.5 (s, 3H), 3.5 (m, 1H), 1.1–2.0 (m, 10H), 0.8 (s, 6H), 0.8 (t, 3H) ppm.

EXAMPLE 46

4-[O-Benzyl-N-(4-cis-tert-butylcyclohexyl) hydroxylamino)-3-ethoxy-2-ethoxymethylpyridine was prepared analogously to Example 2 using 4-O-benzylhydroxylamino-3-ethoxy-2-ethoxymethylpyridine and 4-trans-tert-butyl-1-tosyloxycyclohexane.

Yield: 18.7%

$^1$H-NMR (100 MHz, CDCl$_3$): δ: 8.2 (d, 1H), 7.3 (m, 6H), 4.6 (d, 2H), 4.1 (q, 2H), 3.7 (q, 2H), 3.8 (m, 1H), 1.2–2.1 (m, 15H), 0.8 (s, 9H) ppm.

EXAMPLE 47

4-[O-Benzyl-N-(4-cis-phenylcyclohexyl)hydroxylamino]-3-ethoxy-2-ethoxymethylpyridine was prepared analogously to Example 2 using 4-O-benzylhydroxylamino-3-ethoxy-2-ethoxymethylpyridine (Example 19) and trans-4-phenyl-1-tosyloxycyclohexane.

Yield: 43%

$^1$H-NMR (100 MHz, CDCl$_3$): δ: 8.2 (d, 1H), 7.3 (m, 6H), 4.7 (m, 4H), 4.1 (q, 2H) 3.9 (m, 1H), 3.7 (q, 2H), 2.9 (m, 1H), 1.1–2.3 (m, 14H).

EXAMPLE 48

4-[O-Benzyl-N-(4-cis-(4-ethoxyphenyl)cyclohexyl) hydroxylamino]-3-ethoxy-2-ethoxymethylpyridine was prepared analogously to Example 12 using 4-O-benzylhydroxylamino-3-ethoxy-2-ethoxymethylpyridine (Example 19) and trans-4-(4-ethoxyphenyl)-1-tosyloxycyclohexane.

Yield: 15.9%

$^1$H-NMR (100 MHz, CDCl$_3$): δ: 8.2 (d, 1H), 6.8–7.4 (m, 10H), 4.7 (m, 4H), 3.9–4.2 (m, 5H), 3.7 (q, 2H), 2.9 (m, 1H), 1.2–2.5 (m, 17H) ppm.

EXAMPLE 49

4-[O-Benzyl-N-(4-cis-tert-amylcyclohexyl) hydroxylamino]-3-ethoxy-2-ethoxymethylpyridine was prepared analogously to Example 2 using 4-O-benzylhydroxylamino-3-ethoxy-2-ethoxymethylpyridine (Example 19) and trans-4-tert-amyl-1-tosyloxycyclohexane.

Yield: 24%

$^1$H-NMR (100 MHz, CDCl$_3$): δ: 8.3 (d, 1H), 7.3 (m, 6H), 4.7 (d, 4H), 4.1 (q, 2H), 3.8 (m, 1H), 3.7 (q, 2H), 0.7–2.1 (m, 26H) ppm.

EXAMPLE 50

4-[O-Benzyl-N-(4-butylidenecyclohexyl)] hydroxylamino-3-methoxy-2-methoxymethylpyridine An equimolar amount of butyllithium in hexane is added to 5 g of butyltriphenylphosphonium chloride in 25 ml of dimethoxyethane at 0° C. After 2 hours at 25° C., 5.3 g of 4-[O-benzyl-N-(4-oxocyclohexyl)hydroxylamino]-3-methoxy-2-methoxymethylpyridine (Example 56)are added, and the mixture is stirred for 6 hours. It is then concentrated, and the residue is extracted by shaking with H$_2$O and CH$_2$Cl$_2$. Column purification on silica gel using ethyl acetate/acetone gives 3 g=52.1% of syrup.

$^1$H-NMR (100 MHz, CDCl$_3$): δ: 8.2 (d, 1H), 7.2–7.4 (m, 6H), 5.1 (t, 1H), 4.7 (s, 2H), 4.6 (s, 2H), 3.8 (s, 3H), 3.7 (m, 1H), 3.4 (s, 3H), 1.1–2.7 (m, 12H), 0.9 (t, 3H) ppm.

EXAMPLE 51

4-(4-Butylidenecyclohexyl)amino-3-methoxy-2-methoxymethylpyridine

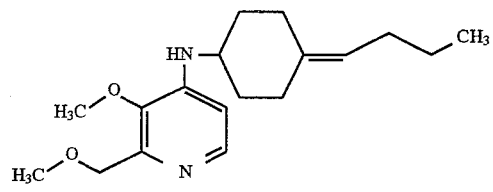

3 g of 4-[O-benzyl-N-(4-butylidenecyclohexyl)] hydroxylamino-3-methoxy-2-methoxymethylpyridine (Example 50)are dissolved in 20 ml of methanol/2 ml of water. 3 g of zinc dust and 12 ml of glacial acetic acid are added. After the mixture has been stirred for 17 hours, it is filtered and the filtrate is concentrated. The residue is extracted by shaking with 2N sodium hydroxide solution and methylene chloride. Purification of the methylene chloride phase by column chromatography over silica gel using ethyl acetate/methanol 5/1 gives 1.8 g=82.2% of oil.

$^1$H-NMR (100 MHz, CDCl$_3$): δ: 8.0 (d, 1H), 6.5 (d, 1H), 5.0–5.3 (m, 1H), 4.6 (m, 1H), 4.5 (s, 2H), 3.8 (s, 3H), 3.7 (s, 3H), 3.4 (m, 1H), 0.8–2.8 (m, 15H) ppm.

EXAMPLE 52

4-[O-Benzyl-N-(4-cis-tert-butylcyclohexyl) hydroxylamino]-3-methoxy-2-allyloxymethylpyridine was prepared analogously to Example 2 using 4-O-benzylhydroxylamino-3-methoxy-2-allyloxymethylpyridine (Example 21) and 4-trans-tert-butyl-1-tosyloxycyclohexane.

$^1$H-NMR (100 MHz, CDCl$_3$): δ: 8.3 (s, 1H), 7.3 (s, 5H), 7.4 (d, 1H), 5.8–6.2 (m, 1H), 5.1–5.4 (m, 2H), 4.7 (d, 2H), 4.1 (m, 2H), 3.9 (s, 3H), 3.8 m (1H), 1.0–2.1 (m, 9H), 0.9 (s, 9H) ppm.

EXAMPLE 53

4-[O-Benzyl-N-(4-cis-phenylcyclohexyl)hydroxylamino]-3-methoxy-2-allyloxymethylpyridine was prepared analogously to Example 2 using 4-O-benzylhydroxylamino-3-methoxy-2-allyloxymethylpyridine (Example 21) and 4-phenyl-1-tosyloxycyclohexane.

Yield: 33.7%

$^1$H-NMR (100 MHz, CDCl$_3$): δ: 8.2 (d, 1H), 7.2 (m, 6H), 5.8–6.2 (m, 1H), 5.1–5.4 (m, 2H), 4.7 (d, 2H), 4.1–4.2 (m, 2H), 3.9 (s, 3H), 3.9 (m, 1H) 2.9 (m, 1H), 1.4–2.3 (m, 8H) ppm.

EXAMPLE 54

4-[O-Benzyl-N-(4-oxocyclohexyl)hydroxylamino]-3-methoxy-3-methoxymethylpyridine 6 g of 4-[O-benzyl-N-(1,4-dioxaspiro[4,5]dec-8-yl)hydroxylamino]-2-methoxy-2-methoxymethylpyridid (Example 29) is allowed to stand for 5 hours with 98% formic acid. The mixture is then concentrated in vacuo and the residue is extracted by shaking with 2N NaOH and methylene chloride. The methylene chloride phase is concentrated. 5.3 g=98.6% yield.

¹H-NMR (100 MHz, CDCl₃): δ: 8.3 (d, 1H), 7.3 (m, 5H), 7.2 (d, 1H), 4.6 (s, 4H), 4.2 (m, 1H), 3.7 (s, 3H), 3.4 (s, 3H), 1.8–2.5 (m, 8H) ppm.

EXAMPLE 55

4-[4-(O-tert-butylhydroxylamino)cyclohexylamino]-3-methoxy-2-methoxymethylpyridine 0.6 g of NaBH₃CN are added to 1.8 g of 4-[4-(O-benzyloximino)cyclohexylamino]-3-methoxy-2-methoxymethylpyridine (Example 57) in 20 ml of methanol, whereupon one spatula-tipful of methyl orange is added. HCl solution in ether is then added dropwise at such a rate that the solution always remains red, during which process the temperature rises to 40° C. After the reaction has ended, the mixture is concentrated, and the residue is extracted by shaking with 2N NaOH and CH₂Cl₂. The CH₂Cl₂ phase is purified over silica gel. 1.9 g=100% yield.

¹H-NMR (100 MHz, CDCl₃): δ: 8.0 (d, 1H), 6.5 (d, 1H), 4.7 (d, 1H), 4.5 (s, 2H), 3.7 (s, 3H), 3.4 (s, 3H), 2.6–2.9 (m, 2H), 1.3–2.1 (m, 8H), 1.2 (m, 9H).

EXAMPLE 56

4-(4-Oxocyclohexylamino]-3-methoxy-2-methoxymethylpyridine 4.4 g of 4-(1,4-dioxaspiro[4,5]dec-8-yl)amino-3-methoxy-2-methoxymethylpyridine (Example 59) is left to stand in 100 ml of 98% formic acid for 17 hours. The mixture is then concentrated, and the residue is extracted by shaking with 2N NaOH and CH₂Cl₂. After the organic phase has been concentrated, 3.4 g=89.9% of crystals are obtained.

¹H-NMR (100 MHz, CDCl₃): δ: 8.1 (d, 1H), 6.5 (d, 1H), 4.6 (d, 1H), 4.5 (s, 2H), 4.1 (m, 1H), 3.8 (s, 3H), 1.8–2.5 (m, 8H) ppm.

EXAMPLE 57

4-[4-(O-tert-butyloximino)cyclohexylamino]-3-methoxy-2-methoxymethylpyridine 3.4 g of 4-(4-oxocyclohexylamino)-3-methoxy-2-methoxymethylpyridine (Example 56) and 5 g of O-tert-butylhydroxylamine hydrochloride are dissolved in 25 ml of methanol. After 8 ml of 30% sodium methylate solution have been added dropwise, the reaction is left to complete, and the solution is then concentrated. The residue is extracted by shaking with H₂O and CH₂Cl₂. When the CH₂Cl₂ phase is concentrated, 4.1 g=94.7% of crystals are obtained.

¹H-NMR (100 MHz, CDCl₃): δ: 8.1 (d, 1H), 6.5 (d, 1H), 4.6 (d, 1H), 4.5 (s, 2H), 3.8 (s, 3H), 3.5 (s, 3H), 3.1 (m, 1H) 1.3–2.5 (m, 8H), 1.3 (s, 9H) ppm.

EXAMPLE 58

4-[4-(O-Benzyloximino)cyclohexylamino]-3-methoxy-2-methoxymethylpyridine

The synthesis was carried out analogously to Example 57 using 4-(4-oxocyclohexylamino)-3-methoxy-2-methoxymethylpyridine (Example 56) and O-benzylhydroxylamine.

Yield: 100%, syrup

¹H-NMR (CDCl₃, 100 MHz): δ: 8.1 (d, 2H), 7.4 (m, 5H), 6.5 (d, 2H), 5.1 (s, 2H), 4.6 (d, 1H), 4.5 (s, 2H), 3.8 (s, 3H), 3.5 (m, 1H), 3.4 (s, 3H), 2.0–2.5 (m, 8H), 1.5 (m, 2H) ppm.

EXAMPLE 59

4-(1,4-Dioxaspiro[4,5]dec-8-yl)amino-3methoxy-2-methoxymethylpyridine

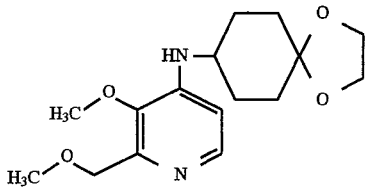

6 g of 4-[O-benzyl-N-(1,4-dioxaspiro[4,5]dec-8-yl)hydroxylamino]-3-methoxy-2-methoxymethylpyridine (Example 29)are hydrogenated in 70 ml of methanol at 50° C. using 5 g of moist Raney nickel. When the required amount of hydrogen has been consumed, the mixture is filtered and concentrated. Purification by column chromatography on silica gel using ethyl acetate/methanol 5/1 gives 3.9 g=98.3% of crystals.

¹H-NMR (100 MHz, CDCl₃): δ: 8.1 (d, 1H), 6.5 (d, 1H), 4.6 (d, 1H), 4.5 (s, 2H), 3.8 (s, 3H), 3.5 (s, 3H), 3.5 (s, 4H), 3.4 (m, 1H), 1.5–2.3 (m, 8H) ppm

EXAMPLE 60

4-(3,3-Dimethyl-1,5-dioxa[5,5]undecan(9)yl)amino-3-methoxy-2-methoxymethylpyridine

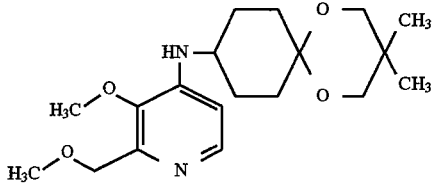

was prepared analogously to (Example 59) using 4-[O-benzyl-N-(3,3-dimethyl-1,5-dioxaspiro[5,5]undecan (9)yl)hydroxylamino]-3-methoxy-2-methoxymethylpyridine (Example 30).

Yield 81.9%

¹H-NMR (100 MHz, CDCl₃): δ: 8.1 (d, 1H), 6.5 (d, 1H), 4.6 (d, 1H), 4.5 (s, 2H), 3.8 (s, 3H), 3.5 (s, 3H), 3.5 (m, 4H), 3.4 (m, 1H), 1.5–2.3 (m, 8H), 1.0 (s, 6H) ppm.

EXAMPLE 61

4-[4-cis-(4-Propoxyphenyl)cyclohexylamino)-3-methoxy-2-methoxymethylpyridine was prepared analogously to Example 5 using 4-[O-benzyl-N-(4-cis-(4-propoxyphenyl)cyclohexyl)hydroxylamino]-3-methoxy-2-methoxymethylpyridine (Example 42).

Yield: 75%

¹H-NMR (100 MHz, CDCl₃): δ: 8.1 (d, 2H), 7.0 (m, 4H), 6.5 (d, 2H), 4.9 (d, 2H), 4.5 (s, 2H), 3.9 (t, 2H), 3.8 (s, 3H), 3.8 (m, 1H), 3.5 (s, 3H), 2.6 (m, 1H), 1.6–2.1 (m, 10H), 1.0 (t, 3H) ppm.

EXAMPLE 62

4-[4-cis-(4-isopropoxyphenyl)cyclohexylamino)-3-methoxy-2-methoxymethoxymethylpyridine was prepared analogously to Example 5 using 4-[O-benzyl-N-(4-cis-(4-isopropoxyphenyl)cyclohexyl) hydroxylamino]-3-methoxy-2-methoxymethylpyridine (Example 43).
Yield: 90%
$^1$H-NMR (100 MHz, CDCl$_3$): δ: 8.1 (d, 1H), 7.0 (m, 4H), 6.5 (d, 1H), 4.9 (d, 1H), 4.5 (s, 2H), 4.5 (m, 1H), 3.8 (s, 3H), 3.7 (m, 1H), 3.5 (s, 3H), 2.6 (m, 1H), 1.6–2.1 (m, 8H), 1.3 (s, 3H), 1.3 (s, 3H) ppm.

EXAMPLE 63

4-[4-cis-(4-Butoxyphenyl)phenylcyclohexylamino)-3-methoxy-2-methoxymethylpyridine was prepared analogously to Example 5 using 4-[O-benzyl-N-(4-cis-(4-butoxyphenyl)cyclohexyl) hydroxylamino]-3-methoxy-2-methoxymethylpyridine (Example 44).
Yield: 89%
$^1$H-NMR (100 MHz, CDCl$_3$): δ: 8.1 (d, 2H), 7.0 (m, 4H), 6.5 (d, 2H), 4.9 (d, 1H), 4.5 (s, 2H), 3.9 (t, 2H), 3.8 (s, 3H), 3.7 (m, 1H), 3.5 (s, 3H), 2.6 (m, 1H), 1.6–2.1 (m, 12H), 1.0 (t, 3H) ppm.

EXAMPLE 64

4-[4-cis-(4-But-2-oxyphenyl)cyclohexylamino)-3-methoxy-2-methoxymethylpyridine was prepared analogously to Example 5 using 4-[O-benzyl-N-(4-cis-(4-but-2-oxyphenyl)cyclohexyl) hydroxylamino]-3-methoxy-2-methoxymethylpyridine (Example 39).
Yield: 84%
$^1$H-NMR (100 MHz, CDCl$_3$): δ: 8.1 (d, 2H), 7.0 (m, 4H), 6.5 (d, 1H), 4.9 (d, 2H), 4.5 (s, 2H), 4.3 (m, 1H), 3.8 (s, 3H), 3.8 (m, 1H), 2.6 (m, 1H), 1.5–2.1 (m, 10H), 1.3 (d, 3H), 1.0 (t, 3H) ppm.

EXAMPLE 65

4-[4-cis-(4-(2-Ethoxyethoxy)phenyl]cyclohexylamino-3-methoxy-2-methoxymethylpyridine was prepared analogously to Example 5 using 4-[O-benzyl-N-(4-cis-4-(2-ethoxyethoxy)phenyl) cyclohexyl)hydroxylamino]-3-methoxy-2-methoxymethylpyridine (Example 40).
Yield: 68%
$^1$H-NMR (100 MHz, CDCl$_3$): δ: 8.1 (d, 2H), 7.0 (q, 4H), 6.5 (d, 2H), 4.9 (d, 1H), 4.5 (s, 2H), 4.0 (m, 4H), 3.9 (m, 1H), 3.8 (s, 3H), 3.6 (q, 2H), 3.5 (s, 3H), 2.6 (m, 1H), 1.6–2.1 (m, 8H), 1.3 (t, 3H) ppm.

EXAMPLE 66

(4-cis-{4-[2-(2-Methoxy-ethoxy)-ethoxy]-phenyl}-cyclohexyl)-(3-methoxy-2-methoxymethyl-pyridine-4-yl)-amine was prepared analogously to Example 5 using O-benzyl-N-(4-cis-{4-[2-(2-methoxy-ethoxy)-ethoxy]-phenyl}-cyclohexyl)-(3-methoxy-2-methoxymethyl-pyridine-4-yl)-hydroxylamine (Example 41)
Yield: 81%
$^1$H-NMR (100 MHz, CDCl$_3$): δ: 8.1 (d, 1H), 7.0 (m, 4H), 6.5 (d, 1H), 4.9 (m, 1H), 4.6 (s, 2H), 3.8 (s, 3H), 4.0 (m, 4H), 3.6 (m, 4H), 3.7 (m, 1H), 3.5 (s, 3H), 3.4 (s, 3H), 2.6 (s, 1H), 1.6–2.1 (m, 8H) ppm.

EXAMPLE 67

4-<4-cis-[4-(2,2-Dimethoxyethoxy)phenyl] cyclohexylamino>-3-methoxy-2-methoxymethylpyridine was prepared analogously to Example 5 using 4-[O-benzyl-N-(4-cis-(4-(2,2-dimethoxyethoxy)phenyl) cyclohexyl)hydroxylamino]-3-methoxy-2-methoxymethylpyridine (Example 38).
Yield: 51%
$^1$H-NMR (100 MHz, CDCl$_3$): δ: 8.1 (d, 1H), 7.0 (m, 4H), 6.5 (d, 1H), 4.9 (d, 1H), 4.7 (t, 1H), 4.5 (s, 2H), 4.0 (d, 2H), 3.8 (s, 3H), 3.7 (m, 1H), 3.5 (s, 3H), 3.5 (s, 6H), 2.6 (m, 1H), 1.6–2.1 (m, 8H) ppm.

EXAMPLE 68

4-[4-cis-(4-Dimethyl-tert-butylsilyloxy)phenyl] cyclohexylamino-3-methoxy-2-methoxymethylpyridine was prepared analogously to Example 5 using 4-[O-benzyl-N-(4-cis-(4-(dimethyl-tert-butylsilyloxy) phenyl)cyclohexyl)hydroxylamino-3-methoxy-2-methoxymethylpyridine. (Example 37)
Yield: 90.0%
$^1$H-NMR (100 MHz, CDCl$_3$): δ: 8.1 (d, 2H), 6.9 (m, 4H), 6.5 (d, 2H), 5.0 (d, 2H), 4.5 (s, 2H), 3.9 (s, 3H), 3.7 (m, 1H), 3.5 (s, 3H), 2.6 (m, 1H), 1.6–2.1 (m, 8H), 1.0 (s, 9H), 0.2 (s, 6H) ppm.

EXAMPLE 69

4-[4-cis-(4-Tetrahydrofur(2)ylmethoxy)phenyl] cyclohexylamino-3-methoxy-2-methoxymethylpyridine was prepared analogously to Example 5 using 4-[O-benzyl-N-4-cis-<(4-tetrahydrofur(2)yl-methoxy) phenyl>-cyclohexylamino]-3-methoxy-2-methoxymethylpyridine (Example 36).
Yield: 89%
$^1$H-NMR (100 MHz, CDCl$_3$): δ: 8.1 (d, 2H), 7.0 (m, 4H), 6.5 (d, 1H), 4.9 (d, 1H), 4.6 (s, 2H), 4.3 (m, 1H), 3.8 (s, 3H), 3.8–4.0 (m, 4H), 3.7 (m, 1H), 3.5 (s, 3H), 2.6 (m, 1H), 1.6–2.1 (m, 12H) ppm.

EXAMPLE 70

4-(Spiro[5.5]undecan(3)yl)amino-3-chloro-2-methoxymethylpyridine

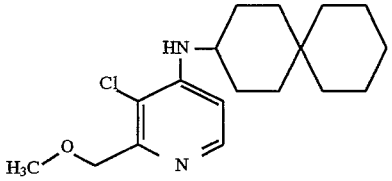

was prepared analogously to Example 51 using 4-[O-benzyl-N-(spiro[5.5]undecan(3)yl-hydroxylamino]-3-chloro-2-methoxymethylpyridine (Example 34).
Yield: 84%
$^1$H-NMR (100 MHz, CDCl$_3$): δ: 8.1 (d, 2H), 6.5 (d, 2H), 4.8 (d, 2H), 4.6 (s, 3H), 3.5 (s, 3H), 3.4 (m, 1H), 1.2–1.9 (m, 18H) ppm.

EXAMPLE 71

4-(Spiro[5.5]undecan(3)yl)amino-3-methoxy-2-methoxymethylpyridine

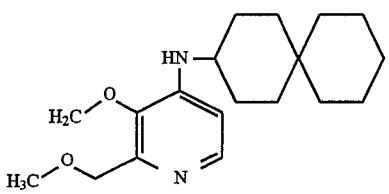

was prepared analogously to Example 5 using 4-[O-benzyl-N-(spiro[5.5]undecan(3)yl)hydroxylamino]-3-methoxy-2-methoxymethylpyridine (Example 33)
Yield: 50.5%
¹H-NMR (CDCl₃, 100 MHz): δ: 8.1 (d, 2H), 6.5 (d, 2H), 4.6 (m, 1H), 4.5 (s, 2H), 3.8 (s, 3H), 3.5 (s, 3H), 3.3 (m, 1H), 1.2–2.0 (m, 18H) ppm.

EXAMPLE 72

4-[cis-(4-(2-(2,5,5-Trimethyl-1,5-dioxan-2-yl)ethoxy)phenyl)cyclohexyl]amino-3-methoxy-2-methoxymethylpyridine

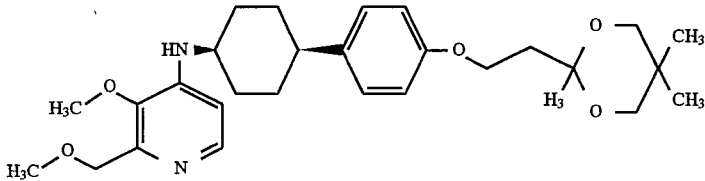

was prepared analogously to Example 5 using 4-]O-benzyl-N-(4-cis-(4-(2-(2,5,5-trimethyl-1,5-dioxan-2yl)ethoxy)phenyl)cyclohexyl)hydroxylamino]-3-methoxy-2-methoxymethylpyridine (Example 35)
Yield 100%
¹H-NMR (100 MHz, CDCl₃): δ: 8.1 (d, 1H), 7.0 (m, 4H), 6.5 (d, 2H), 4.9 (d, 1H), 4.5 (s, 2H), 4.1 (t, 2H), 3.8 (s, 3H), 3.8 (m, 1H), 3.5 (m, 4H), 3.5 (s, 3H), 2.6 (m, 1H), 1.6–2.4 (m, 10H), 1.4 (s, 3H), 1.0 (s, 3H), 0.9 (s, 3H) ppm.

EXAMPLE 73

4-[4-cis-(4-(2-oxoethoxy)phenyl)cyclohexyl]amino-3-methoxy-2-methoxymethylpyridine
was prepared analogously to Example 56 using 4-[O-benzyl-N-(4-cis-(4-(2,2-dimethoxy)phenyl)cyclohexyl)hydroxylamino]-3-methoxy-2-methoxymethylpyridine (Example 67).
Yield: 90.4%
¹H-NMR (100 MHz, CDCl₃): δ: 9.9 (s, 1H), 8.1 (d, 1H), 7.0 (m, 4H), 6.5 (d, 1H), 4.9 (d, 1H), 4.5 (d, 2H), 3.9 (s, 3H), 3.8 (m, 1H), 3.5 (s, 3H), 2.6 (m, 1H), 1.6–2.1 (m, 8H) ppm.

EXAMPLE 74

4-(4-cis-tert-Butylcyclohexylamino)-3-ethoxy-2-ethoxymethylpyridine
was prepared analogously to Example 5 using 4-[O-benzyl-N-(4-cis-tert-butylcyclohexyl)hydroxylamino]-3-ethoxy-2-ethoxymethylpyridine (Example 46)
Yield: 80%
¹H-NMR (100 MHz, CDCl₃): δ: 8.1 (d, 1H), 6.4 (d, 1H), 4.9 (d, 1H), 4.5 (s, 1H), 4.0 (q, 2H), 3.8 (q, 2H), 3.7 (m, 1H), 1.1–2.1 (m, 15H), 0.9 (s, 3H).

EXAMPLE 75

4-(4-cis-tert-Amylcyclohexylamino)-3-ethoxy-2-ethoxymethylpyridine was prepared analogously to Example 5 using 4-[O-benzyl-N-(4-cis-tert-amylcyclohexyl)hydroxylamino]-3-ethoxy-2-ethoxymethylpyridine (Example 49)
Yield: 81%
¹H-NMR (100 MHz, CDCl₃): δ: 8.1 (d, 1H), 6.4 (d, 1H), 4.8 (d, 1H), 4.5 (s, 2H), 3.9 (q, 2H), 3.7 (m, 1H), 3.7 (q, 2H), 1.1–2.0 (m, 18H), 0.8 (s, 6H), 0.8 (t, 3H).

EXAMPLE 76

4-(4-cis-Phenylcyclohexyl)amino-3-ethoxy-2-ethoxymethylpyridine
was prepared analogously to Example 5 using 4-[O-benzyl-N-(4-cis-phenylcyclohexyl)hydroxylamino]-3-ethoxy-2-ethoxymethylpyridine (Example 47).
Yield: 53%
¹H-NMR (100 MHz, CDCl₃): δ: 8.1 (d, 1H), 7.1–7.4 (m, 5H), 6.4 (d, 1H), 5.0 (d, 1H), 4.5 (s, 2H), 4.0 (q, 2H), 3.8 (m, 1H), 3.7 (q, 2H), 2.7 (m, 1H), 1.5–2.1 (m, 8H), 1.2 (t, 3H) ppm, 1.5 (t, 3H) ppm.

EXAMPLE 77

4-[4-cis-(4-Ethoxyphenyl)cyclohexylamino]-3-ethoxy-2-ethoxymethylpyridine
was prepared analogously to Example 5 using 4-[O-benzyl-N-(4-cis-(4-ethoxyphenyl)cyclohexyl)hydroxylamino]-3-ethoxy-2-ethoxymethylpyridine (Example 48).
Yield: 76.3%
¹H-NMR (100 MHz, CDCl₃): δ: 8.1 (d, 1H), 6.7–7.2 (m, 4H), 6.5 (d, 1H), 5.0 (d, 1H), 4.6 (s, 2H), 4.0 (q, 2H), 3.8 (m, 1H), 3.7 (q, 2H), 2.5 (m, 1H), 1.2–2.1 (m, 17H) ppm.

EXAMPLE 78

4-(4-cis-Phenylcyclohexylamino)-2-allyloxymethyl-3-methoxypyridine
was prepared analogously to Example 50 using 4-[O-benzyl-N-(4-cis-phenylcyclohexyl)hydroxylamino]-3-methoxy-2-allyloxymethylpyridine (Example 53).
Yield: 99.0%
¹H-NMR (100 MHz, CDCl₃): δ: 8.1 (d, 1H), 7.2 (m, 6H), 6.5 (d, 1H), 5.8–6.2 (m, 1H), 5.1–5.4 (m, 2H), 4.9 (d, 1H), 4.6 (s, 2H), 4.1–4.2 (m, 2H), 3.8 (s, 3H), 3.7 (m, 1H), 2.5–2.8 (m, 1H), 1.5–2.1 (m, 8H) ppm.

EXAMPLE 79

4-(4-cis-tert-Butylcyclohexylamino)-2-allyloxymethyl-3-methoxypyridine
was prepared analogously to Example 50 using 4-[O-benzyl-N-(4-cis-tert-butylcyclohexyl)hydroxylamino]-3-methoxy-1-allyloxymethylpyridine (Example 52)
Yield: 79.1%
¹H-NMR (100 MHz, CDCl₃): δ: 8.1 (d, 1H), 7.2 (m, 6H), 6.5 (d, 1H), 5.8–6.2 (m, 1H), 5.1–5.4 (m, 2H), 4.9 (d, 1H), 4.6 (s, 2H), 4.1–4.2 (m, 2H), 3.8 (s, 3H), 3.7 (m, 1H), 2.5–2.8 (m, 1H), 1.5–2.1 (m, 8H) ppm.

EXAMPLE 80

4-(4-cis-tert-Butylcyclohexyl)amino-2-methoxymethylpyridine was prepared analogously to Example 50 using 4-[O-benzyl-N-(4-cis-tert-butylcyclohexyl)hydroxylamino]-3-bromo-2-methoxymethylpyridine (Example 31)

Yield: 36%

$^1$H-NMR (100 MHz, CDCl$_3$): δ: 8.1 (d, 1H), 6.6 (d, 2H), 6.4 (q, 1H), 4.5 (s, 2H), 4.4 (d, 1H), 3.7 (m, 1H), 3.5 (s, 3H), 1.0–2.0 (m, 8H), 0.8 (s, 9H) ppm.

EXAMPLE 81

4-(4-cis-Phenylcyclohexylamino)-2-methoxymethylpyridine was prepared analogously to Example 50 using 4-[O-benzyl-N-(4-cis-phenylcyclohexyl)hydroxylamino]-3-bromo-2-methoxymethylpyridine (Example 32).

Yield: 38%

$^1$H-NMR (100 MHz, CDCl$_3$): δ: 8.2 (d, 1H), 7.2 (m, 5H), 6.6 (d, 1H), 6.4 (q, 1H), 4.5 (s, 2H), 4.5 (m, 1H), 3.8 (m, 1H), 3.5 (s, 3H), 2.6 (m, 1H), 1.6–2.1 (m, 8H) ppm.

EXAMPLE 82

4-[4-cis-(2,2-Dimethylpropyl)cyclohexylamino]-2-methoxypyridine was prepared analogously to Example 50 using 4-[O-benzyl-N-(4-cis-tert-amylcyclohexyl)hydroxylamino]-3-bromo-2-methoxypyridine (Example 45)

Yield: 52.3%

$^1$H-NMR (100 MHz, CDCl$_3$): δ: 8.1 (d, 1H), 6.6 (d, 1H), 6.3 (q, 1H), 4.5 (s, 2H), 4.4 (d, 1H), 3.7 (m, 1H), 3.5 (s, 3H), 1.1–1.6 (m, 11H), 0.8 (t, 3H), 0.8 (s, 6H) ppm.

EXAMPLE 83

3-Bromo-4-(4-cis-tert-butylcyclohexylamino)-2-methoxymethylpyridine was prepared by reacting 4-[O-benzyl-N-(4-cis-tert-butylcyclohexyl)hydroxylamino]-3-bromo-2-methoxymethylpyridine (Example 31) with a Ti(O) solution analogously to the process described by M. Malinowski and L. Kaczmarek, Journal f. prakt. Chemie 330 (1988) 154.

Yield: 30%

$^1$H-NMR (100 MHz, CDCl$_3$): δ: 8.2 (d, 1H), 6.4 (d, 1H), 5.2 (d, 1H), 4.6 (s, 2H), 3.6 (s, 3H), 3.8 (m, 1H), 1.1–2.0 (m, 9H), 0.8 (s, 3H) ppm.

EXAMPLE 84

3-Chloro-4-[cis-(4-tert-butyl)cyclohexylamino]-2-methoxymethylpyridine 1 g of 2-Methoxymethyl-3,4-dichloropyridine and 1 g of cis-4-tert-butylcyclohexylamine together with 4.3 mg of ammonium chloride are heated for 3.5 hours at 180° C. in 4 ml of N-methylpyrrolidone. The batch is then poured into saturated bicarbonate solution, and ethyl acetate is added to the product. The ethyl acetate phase is washed 3 times using water and subsequently chromatographed over silica gel using ethyl acetate/hexane 1:1 as eluent.

Yield: 47%, oil.

$^1$H-NMR (100 MHz, CDCl$_3$): δ: 8.1 (d, 1H), 6.5 (d, 1H), 5.1 (d, 1H), 4.6 (s, 2H), 3.5 (s, 3H), 3.7 (m, 1H), 1.0–2.0 (m, 9H), 0.9 (s, 9H) ppm.

EXAMPLE 85

3-Chloro-4-[4-cis-but(2)yl-cyclohexylamino]-2-methoxymethylpyridine was prepared analogously to Example 84 using 2-methoxymethyl-3,4-dichloropyridine and 4-cis-but(2)yl-cyclohexylamine.

Yield: 40%

$^1$H-NMR (100 MHz, CDCl$_3$): δ: 8.1 (d, 1H), 6.5 (d, 1H), 5.1 (d, 1H), 4.6 (s, 2H), 3.7 (m, 1H), 3.5 (s, 3H), 1.0–2.0 (m, 12H), 0.9 (t, 3H), 0.9 (d, 3H) ppm.

EXAMPLE 86

3-Chloro-4-[4-trans-but(2)yl-cyclohexylamino]-2-methoxymethylpyridine was prepared analogously to Example 84 using 2-methoxymethyl-3,4-dichloropyridine and 4-trans-but(2)yl-cyclohexylamine.

Yield: 38%

$^1$H-NMR (100 MHz, CDCl$_3$): δ: 8.1 (d, 1H), 6.5 (d, 1H), 5.0 (d, 1H), 4.6 (s, 2H), 3.7 (m, 1H), 3.5 (s, 3H), 1.0–2.0 (m, 12H), 0.9 (t, 3H), 0.9 (d, 3H) ppm.

EXAMPLE 87

3-Chloro-4-[4-cis-cyclohexylcyclohexylamino]-2-methoxymethylpyridine was prepared analogously to Example 84 using 2-methoxymethyl-3,4-dichloropyridine and 4-cis-cyclohexylcyclohexylamine.

Yield: 35%

$^1$H-NMR (100 MHz, CDCl$_3$): δ: 8.1 (d, 1H), 6.5 (d, 1H), 5.1 (d, 1H), 4.6 (s, 2H), 3.7 (m, 1H), 3.5 (s, 3H), 0.9–2.0 (m, 20H) ppm.

EXAMPLE 88

3-Chloro-4-[4-trans-cyclohexylcyclohexylamino]-2-methoxymethylpyridine was prepared analogously to Example 84 using 2-methoxymethyl-3,4-dichloropyridine and 4-trans-cyclohexylcyclohexylamine.

Yield: 17%

$^1$H-NMR (100 MHz, CDCl$_3$): δ: 8.1 (d, 1H), 6.5 (d, 1H), 4.7 (d, 1H), 4.6 (s, 2H), 3.5 (s, 3H), 3.2 (m, 1H), 0.9–2.2 (m, 20H) ppm.

EXAMPLE 89

3-Chloro-4-[4-cis(1,1,3,3-tetramethylbutyl)cyclohexylamino]-2-methoxymethylpyridine
and

EXAMPLE 90

3-Chloro-4-[4-trans-(1,1,3,3-tetramethylbutyl)cyclohexylamino]-2-methoxymethylpyridine were prepared analogously to Example 84 using 2-methoxymethyl-3,4-dichloropyridine and cis/trans-4-(tetramethylbutyl)cyclohexylamine, followed by isomer separation on ®Sephadex using methanol.

Yield (trans isomer): 17%

Yield (cis isomer): 17%

$^1$H-NMR (100 MHz, CDCl$_3$) (trans isomer): δ: 8.1 (d, 1H), 6.5 (d, 1H), 4.7 (d, 1H), 4.6 (s, 2H), 3.5 (s, 3H), 3.2 (m, 1H), 1.1–2.2 (m, 11H), 1.0 (s, 6H), 1.0 (s, 9H) ppm.

$^1$H-NMR (100 MHz, CDCl$_3$) (cis isomer): δ: 8.1 (d, 1H), 6.5 (d, 1H), 5.1 (d, 1H), 4.6 (s, 2H), 3.8 (m, 1H), 3.5 (s, 3H), 1.2–2.0 (m, 11H), 1.0 (s, 9H), 0.9 (s, 6H) ppm.

EXAMPLE 91

3-Chloro-4-(3-cis-isoamylcyclopentyl)amino-2-methoxymethylpyridine was prepared analogously to Example 89 using 2-methoxymethyl-3,4-dichloropyridine and 3-isoamylcyclopentylamine.

Yield: 39%

¹H-NMR (100 MHz, CDCl₃): δ: 8.1 (d, 1H), 6.5 (d, 1H), 4.8 (d, 1H), 4.6 (s, 2H), 3.8 (m, 1H), 3.4 (s, 3H), 1.0–2.2 (m, 9H), 0.8 (t, 3H), 0.8 (s, 6H) ppm.

EXAMPLE 92

3-Chloro-4-[4-(4-(2-ethoxyethoxy) ethoxy)phenyl] cyclohexylamino-2-methoxymethylpyridine was prepared analogously to Example 84 using 2-methoxymethyl-3,4-dichloropyridine and 4-[4-(2-ethoxyethoxy)ethoxy]phenylcyclohexylamine.

Yield: 40%

¹H-NMR: 8.2 (d, 1H), 7.0 (m, 4H), 6.5 (d, 1H), 5.1 (d, 1H), 4.6 (s, 2H), 3.4–4.2 (m, 14H), 1.1–2.6 (m, 9H), 1.2 (t, 3H) ppm.

EXAMPLE 93

3-Chloro-4-[2-(2,4-dimethyl)phenoxy]propylamino-2-methoxymethylpyridine was prepared analogously to Example 84 using 2-methoxymethyl-3,4-dichloropyridine and 2-(2,4-dimethyl)phenoxypropylamine.

Yield: 34%

¹H-NMR: (100 MHz, CDCl₃): δ: 8.2 (d, 1H), 6.6–7.0 (m, 4H), 6.5 (d, 1H), 5.3 (m, 1H), 4.6 (s, 2H), 4.4–4.6 (m, 14H), 3.5 (s, 3H), 3.3–3.5 (m, 2H), 2.2 (d, 6H), 1.4 (d, 3H) ppm.

EXAMPLE 94

3-Chloro-4-[1-(4-difluoromethoxyphenyl)]propylamino-2-methoxymethylpyridine was prepared analogously to Example 84 using 2-methoxymethyl-3,4-dichloropyridine and 1-(4-difluoromethoxyphenyl)-propylamine.

Yield: 27%

¹H-NMR: (100 MHz, CDCl₃): δ: 8.0 (d, 1H), 7.2 (q, 4H), 6.5 (t, 1H), 6.2 (d, 1H), 5.2 (d, 1H), 4.6 (s, 2H), 4.3 (m, 1H), 3.5 (s, 3H), 1.9 (m, 2H), 1.0 (t, 3H) ppm.

EXAMPLE 95

3-Chloro-[4-[2-methyl-3-(4-tert-butylphenyl)]-propylamino-2-methoxymethylpyridine was prepared analogously to Example 84 using 2-methoxymethyl-3,4-dichloropyridine and 2-methyl-3-(4-tert-butylphenyl)-propamine.

Yield: 54%

¹H-NMR: (100 MHz, CDCl₃): δ: 8.1 (d, 1H), 7.2 (m, 4H), 6.3 (d, 1H), 4.9 (m, 1H), 4.6 (s, 2H), 3.5 (s, 3H), 3.1 (m, 2H), 2.5–2.7 (m, 2H), 1.9–2.2 (m, 1H), 1.3 (s, 9H), 1.0 (d, 3H) ppm.

EXAMPLE 96

3-Chloro-4-[2-(2,3-dimethyl-4-ethoxyethylphenoxy)] ethylamino-2-methoxymethylpyridine was prepared analogously to Example 84 using 2-methoxymethyl-3,4-dichloropyridine and 2-(2,3-dimethyl-4-ethoxyethyl)phenoxyethylamine.

Yield: 13%

¹H-NMR: (100 MHz, CDCl₃): δ: 8.2 (d, 1H), 6.8 (q, 2H), 6.3 (d, 1H), 5.4 (m, 1H), 4.6 (s, 2H), 4.2 (t, 2H), 3.4–3.7 (m, 8H), 3.5 (s, 3H), 2.8–3.0 (m, 2H), 2.2 (s, 3H), 2.2 (s, 3H), 1.2 (t, 3H) ppm.

EXAMPLE 97

3-Chloro-4-[cis-4-butylcyclohexyl]amino-2-methoxymethylpyridine
and

EXAMPLE 98

3-Chloro-4-[trans-4-butylcyclohexyl]amino-2-methoxymethylpyridine were prepared analogously to Example 89/90 using 2-methoxymethyl-3,4-dichloropyridine and 4-cis/trans-butylcyclohexylamine.

Yield: 12% (cis isomer)

¹H-NMR: (100 MHz, CDCl₃): δ: 8.1 (d, 1H), 6.4 (d, 1H), 5.0 (d, 1H), 4.6 (s, 2H), 3.7 (m, 1H), 3.5 (s, 3H), 1.0–1.9 (m, 15H), 0.9 (t, 3H) ppm
and Yield: 9% (trans isomer)

¹H-NMR: (100 MHz, CDCl₃): δ: 8.1 (d, 1H), 6.5 (d, 1H), 4.7 (d, 1H), 4.6 (s, 2H), 3.5 (s, 3H), 3.2 (m, 1H), 1.0–2.2 (m, 15H), 0.9 (t, 3H) ppm.

EXAMPLE 99

3-Chloro-4-[2-methyl-3-(4-isopropylphenyl)] propylamino-2-methoxymethylpyridine was prepared analogously to Example 84 using 2-methoxymethyl-3,4-dichloropyridine and 2-methyl-3 (4-isopropylphenyl)propylamine.

Yield: 33%

¹H-NMR: (100 MHz, CDCl₃): δ: 8.1 (d, 2H), 7.1 (m, 4H), 6.3 (d, 1H), 4.9 (m, 1H), 4.6 (s, 2H), 3.5 (s, 3H), 2.0–3.2 (m, 6H), 1.2 (d, 6H), 1.0 (d, 3H) ppm.

EXAMPLE 100

3-Chloro-4-[4-(4-fluorobenzylidene)cyclohexyl]amino-2-methoxymethylpyridine

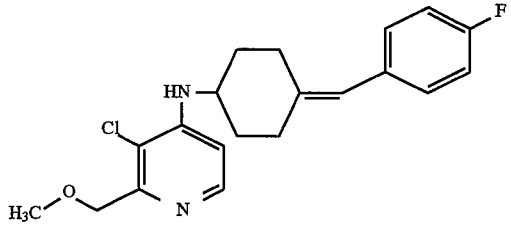

was prepared analogously to Example 84 using 2-methoxymethyl-3,4-dichloropyridine and 4-[4-(4-fluorobenzylidene)]cyclohexylamine.

Yield: 39%

¹H-NMR: (100 MHz, CDCl₃): δ: 8.1 (d, 1H), 7.1 (m, 4H), 6.5 (d, 1H), 6.3 (s, 1H), 4.8 (d, 1H), 4.6 (s, 2H), 3.6 (m, 1H), 3.5 (s, 3H), 1.2–2.9 (m, 8H) ppm.

EXAMPLE 101

3-Chloro-4-[4-cis-(1-cyclohexyl-1-trifluoromethyl-2,2,2-trifluoroethyl)cyclohexyloxy]-2-methoxymethylpyridine was prepared analogously to Example 11 using 2-methoxymethyl-3,4-dichloropyridine and 4-cis-(1-cyclohexyl-1-trifluoromethyl-2,2,2-trifluoroethyl) cyclohexanol.

Yield: 11%

¹H-NMR: (100 MHz, CDCl₃): δ: 8.3 (d, 1H), 6.9 (d, 1H), 4.7 (m, 1H), 4.7 (s, 2H), 3.5 (s, 3H), 1.1–2.3 (m, 20H) ppm.

EXAMPLE 102

3-Chloro-4-[4-cis-(1-cyclohexyl-1-methylethyl) cyclohexyloxy]-2-methoxymethylpyridine was prepared analogously to Example 11 using 2-methoxymethyl-3,4-dichloropyridine and 4-cis(1-cyclohexyl-1-methylethyl)cyclohexyloxy]-2-methoxymethylpyridine.

Yield: 23%

$^1$H-NMR: (100 MHz, CDCl$_3$): δ: 8.3 (d, 1H), 6.8 (d, 1H), 4.7 (m, 1H), 4.6 (s, 2H), 3.5 (s, 3H), 0.8–2.1 (m, 20H), 0.8 (s, 6H) ppm.

EXAMPLE 103

2-Methoxy-3-cyano-4-(cis-4-tert-butylcyclohexylamino)pyridine 0.93 g (6.26 mmol) of trimethyloxonium tetrafluoroborate is added to 1.63 g (5.96 mmol) of 3-cyano-4-(cis-4-tert-butylcyclohexylamino)pyrid-2-one in 30 ml of methylene chloride, and the mixture is stirred for 75 minutes at room temperature. After the addition of 10 g of ice and 5 ml of 2N sodium hydroxide and after evaporation of the methylene chloride, the reaction product is extracted using ethyl acetate. It is purified by column chromatography.

Yield: 1.25 g (73%); R$_f$=0.51 (Diisopropyl ether) M.p. 113° C.

$^1$H-NMR: (CDCl$_3$): δ: 7.90 (d, 1H), 6.22 (d, 1H), 5.16 (d, 1H), 3.80 (m, 1H), 4.0 (s, 3H), 1.0–2.0 (m, 9H), 0.90 (s, 9H) ppm.

EXAMPLE 104

2-Chloro-3-cyano-4-(cis-4-tert-butylcyclohexylamino)pyridine 5 ml of phosphorus oxychloride and 3 drops of dimethylformamide are added to 0.4 g (1.46 mmol) of 3-cyano-4-(cis-4-tert-butylcyclohexylamino)pyrid-2-ine and the mixture is refluxed for 3 hours. The excess phosphorus oxychloride is subsequently distilled off in vacuo, the residue is treated with ice-water, the aqueous solution is brought to pH 7.5–8 using 32% sodium hydroxide solution, and the reaction product was extracted using ethyl acetate. The product is purified by column chromatography.

Yield: 0.24 g (56%); R$_f$=0.35 (diisopropyl ether) M.p. 150° C.

$^1$H-NMR: (CDCl$_3$): δ: 8.06 (d, 1H), 6.48 (d, 1H), 5.34 (d, 1H), 3.80 (m, 1), 1.0–2.0 (m, 9H), 0.88 (s, 9H), ppm.

EXAMPLE 105

2-Methoxy-3-cyano-4-n-octylaminopyridine as Example 103, using 3-cyano-4-n-octylaminopyrid-2-one Yield: 55%; m.p.=104° C.

$^1$H-NMR (CDCl$_3$): δ: 7.91 (d, 1H), 6.22 (d, 1H), 5.00 (m, 1H), 3.98 (s, 3H), 3.23 (m, 2H), 1.2 to 1.8 (m, 12H), 0.88 (t, 3H) ppm

EXAMPLE 106

2-Chloro-3-cyano-4-n-octylaminopyridine as Example 104, using 3-cyano-4-n-octylaminopyrid-2-one Yield: 87%; m.p.=85° C.

$^1$H-NMR (CDCl$_3$): δ: 8.06 (d, 1H), 6.50 (d, 1H, 5.45 (m, 1H), 3.28 (m, 2H), 1.2 to 1.8 (m, 12H), 0.88 (t, 3H)

EXAMPLE 107

2-Methoxy-3-cyano-4-(cis-4-phenylcyclohexylamino)pyridine as Example 103, using 3-cyano-4-(cis-4-phenylcyclohexylamino)pyrid-2-one Yield: 80%

$^1$H-NMR (CDCl$_3$): δ: 7.92 (d, 1H), 7.18 to 7.38 (m, 5H), 6.28 (d, 1H), 5.24 (d, 1H), 3.98 (s, 3H), 3.87 (m, 1H), 2.63 (m, 1H), 1.6 to 2.05 (m, 8H) ppm

EXAMPLE 108

2-Chloro-3-cyano-4-(cis-4-phenylcyclohexylamino)pyridine as Example 104, using 3-cyano-4-(cis-4-phenylcyclohexylamino)pyrid-2-one Yield: 85%

$^1$H-NMR (CDCl$_3$): δ: 8.08 (d, 1H), 7.16 to 7.36 (m, 5H), 6.55 (d, 1H), 5.40 (d, 1H), 3.88 (m, 1H), 2.66 (m, 1H), 1.60 to 2.10 (m, 8H) ppm

B. Formulation Examples a) A dust is obtained by mixing 10 parts by weight of active substance and 90 parts by weight of talc as inert substance and comminuting the mixture in a hammer mill.

b) A wettable powder which is readily dispersible in water is obtained by mixing 25 parts by weight of active substance, 65 parts by weight of kaolin-containing quartz as inert substance, 10 parts by weight of potassium lignin sulfonate and 1 part by weight of sodium oleylmethyltaurinate as wetting agent and dispersant and grinding the mixture in a pinned-disk mill.

c) A dispersion concentrate which is readily dispersible in water is prepared by mixing 40 parts by weight of active substance with 7 parts by weight of a sulfosuccinic monoester, 2 parts by weight of a sodium ligninsulfonate and 51 parts by weight of water, and grinding the mixture in a ball mill to a fineness of below 5 microns.

d) An emulsifiable concentration can be prepared with 15 parts by weight of active substance, 75 parts by weight of cyclohexanone as the solvent and 10 parts by weight of oxethylated nonylphenyl (10 AeO) as emulsifier.

e) Granules can be prepared with 2 to 15 parts by weight of active substance and an inert granule carrier, such as attapulgite, pumice granules and/or quartz sand. It is expedient to use a suspension of the wettable powder of Example b) with a solids content of 30%, and this is sprayed onto the surface of attapulgite granules, dried and mixed intimately. The percentage by weight of the wettable powder is approximately 5 and that of the inert carrier material approximately 95% of the finished granules.

C. Biological Examples

Example 1

*Phytophthora infestans*

Tomato plants cv. "Rheinlands Ruhm" at the 3- to 4-leaf stage were wetted uniformly to runoff point using aqueous suspensions of the claimed compounds. After the spray coating had dried on, the plants were inoculated with a zoosporangia suspension of *Phytophthora infestans* and kept for 2 days in a controlled-environment cabinet under ideal infection conditions. Then, the plants were grown on in a greenhouse until the symptoms became visible. The diseased plants were scored approximately 1 week after inoculation. The disease level of the plants was expressed in percent diseased leaf area compared with the untreated control plants, which showed the disease level of 100%.

At 250 mg of active substance/1 of spray mixture, the following substance inhibits the disease completely:

Compound of Example 6

Example 2

*Plasmopara viticola*

Vine seedlings cvs. "Riesling/Ehrenfelder" approximately 6 weeks after sowing were treated at runoff point using aqueous suspensions of the claimed compounds. After the spray coating had dried on, the plants were inoculated with a zoosporangia suspension of *Plasmopara viticola*, and the dripping wet plants were placed into a controlled-environment cabinet at 23° C. under relative atmospheric humidity of 80 to 90% for 4 to 5 hours.

After an incubation time of 7 days in a greenhouse, the plants were returned overnight to the controlled-environment cabinet to stimulate sporulation of the fungus. Then, the disease was evaluated. The disease level of the plants was expressed in percent diseased leaf area compared with the untreated control plants, which showed the disease level of 100%.

At 250 mg of active substance/1 of spray mixture, the following substance inhibits the disease completely:

Compound of Example 5

Example 3

*Pyrenophora teres*

Barley plants cv. "Igri" at the 2-leaf stage were treated to runoff point with an aqueous suspension of the claimed compounds. After the spray coating had dried on, the plants were inoculated with an aqueous spore suspension of *Pyrenophora teres* and incubated for 16 hours in a controlled-environment cabinet at a relative atmospheric humidity of 100%. The infected plants were then grown on in a greenhouse at 25° C. under relative atmospheric humidity of 80%.

Approximately 1 week after inoculation, the incidence of disease was evaluated, and the disease level was scored in percent diseased leaf area in comparison with untreated controls, which showed an infection level of 100%.

At 250 mg of active substance/1 of spray mixture, the following substance inhibits the disease completely:

Compound of Example 18

Example 4

*Erysiphe graminis*

Barley plants at the 3-leaf stage were severely inoculated with conidia of powdery mildew of barley (*Erysiphe graminis* f. sp. hordei) and placed in a greenhouse at 20° C. and a relative atmospheric humidity of 90 to 95%. 24 hours after inoculation, the plants were wetted uniformly with the compounds listed below, the active substance concentrations being as shown. After an incubation time of 10 days, the plants were examined for incidence of powdery mildew of barley. The disease level of the plants was expressed on percent diseased leaf area compared with the untreated control plants, which showed the disease level of 100%.

At 250 mg of active substance/1 of spray mixture, the following substances inhibit the disease completely:

Compound of Example 6 and Example 5

Example 5

Bean plants (Phaseolus v.) which were severely infested with the two-spotted spider mite (*Tetranychus urticae*, full population) were sprayed with an aqueous dilution of a wettable powder concentrate containing 250 ppm of the active substance in question.

The mortality of the mites was checked after 7 days. A destruction rate of 100% was achieved using the compounds of Examples 5 and 11.

Example 6

Field beans (*Vicia faba*) which were heavily populated with the bean aphid (*Aphis fabae*) are sprayed with aqueous dilutions of wettable powder concentrates containing 250 ppm of active substance until the stage of runoff is just reached. The mortality of the aphids is determined for 3 days. A destruction rate of 100% can be achieved with the compounds of Examples 6 and 5.

Example 7

Bean plants which are heavily populated with white fly (*Trialeurodes vaporariorum*) were sprayed with aqueous suspensions of wettable powder concentrates (250 ppm of active substance content) until the stage of runoff was just reached. After the plants had been placed in a greenhouse, they were checked under the microscope after 14 days, resulting in a 100% mortality rate in each of the preparations with the active substances of Examples 6, 5 and 11.

Example 8

L3 larvae of the beetle species *Diabrotica undecimpunctata* were placed onto filter paper disks, each of which had absorbed 2 ml of an aqueous dilution of a wettable powder concentrate containing 250 ppm of active substance, and they were kept for 3 days in sealed Petri dishes at room temperature (23° C.). Then, the mortality of the larvae was checked.

A destruction rate of 100% was achieved with compounds of Examples 6 and 5.

Example 9

24-hour old imagines of the common housefly (*Musca domestica*) were placed into glass Petri dishes. Bottom and lid had been coated with in each case 2 ml of an aqueous dilution of a wettable powder concentrate containing 250 ppm of active substance. This had been allowed to dry in the air to give a coating on the glass surfaces.

3 hours after the animals had been introduced and the dishes had been sealed, the mortality was checked.

The destruction rate of 100% was achieved with the compound of Example 18.

We claim:

1. A compound of the formula 1 or salt thereof,

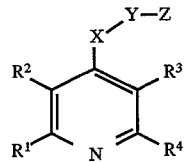

in which
(1) the number x of the radicals $R^1$, $R^2$, $R^3$ and $R^4$, which are identical or different, is selected from the group consisting of
R—O—CH$_2$—,
halo(C$_1$–C$_4$)alkoxymethyl, halo($C_1$–$C_4$)alkenyloxymethyl,
and x is 1, 2, 3, or 4;

and the remaining 4-x radicals $R^1$, $R^2$, $R^3$, and $R^4$, which are identical or different, are selected from the group consisting of
($C_1$–$C_4$)alkyl,
($C_2$–$C_4$)alkenyl,
($C_1$–$C_4$)alkoxy,
($C_2$–$C_4$)alkenyloxy,
halo($C_1$–$C_4$)alkyl,
halo($C_2$–$C_4$)alkenyl,
halo($C_1$–$C_4$)-alkoxy,
halo($C_2$–$C_4$)alkenyloxy,
($C_1$–$C_4$)alkylthio,
($C_1$–$C_4$)alkylsulfinyl,
($C_1$–$C_4$)alkylsulfonyl,
aryl,
substituted amino,
halogen and hydrogen;

R is ($C_1$–$C_{10}$)alkyl,
($C_2$–$C_{10}$)alkenyl,
($C_2$–$C_{10}$)alkynyl,
($C_3$–$C_8$)cycloalkyl or aralkyl;

Arylkyl is aryl($C_1$–$C_4$)alkyl;

(2) X is NH, NR or NOR and R is as defined above under (1);

(3) Y is a bond or a bivalent hydrocarbon radical having 1 to 6 carbon atoms which is substituted by one to three, identical or different radicals selected from the series consisting of
($C_1$–$C_7$)alkyl,
($C_2$–$C_4$)alkenyl,
($C_3$–$C_7$)alkynyl,
($C_3$–$C_7$)cycloalkyl,
($C_3$–$C_7$)cycloalkenyl,
halogen,
halo($C_1$–$C_4$)alkyl,
halo($C_1$–$C_4$)-alkoxy,
hydroxyl and
($C_1$–$C_4$)acyl; and (4) z is
($C_3$–$C_8$)cycloalkyl or ($C_5$–$C_8$)cycloalkenyl, and the ($C_3$–$C_8$)cycloalkyl or ($C_5$–$C_8$)cycloalkenyl radical is substituted by one or more, identical or different radicals selected from the series consisting of
($C_1$–$C_{18}$)alkyl,
($C_2$–$C_{18}$)alkenyl,
($C_1$–$C_{12}$)alkoxy,
($C_2$–$C_{12}$)acyl,
($C_1$–$C_{12}$)alkyloxycarbonyl,
$SiR^9R^{10}R^{11}$,
$NR^{16}R^{17}$,
hydroxyl,
oxo,
halogen,
aryl,
($C_1$–$C_{18}$)alkanediyl,
($C_1$–$C_{19}$)alkanediyldioxy,
($C_1$–$C_{13}$)alkyoximino,
aryl($C_1$–$C_4$)alkyloximino, and
($C_2$–$C_{18}$)alkylidene and, in the abovementioned ($C_1$–$C_{18}$), ($C_2$–$C_{18}$), ($C_1$–$C_{12}$), ($C_2$–$C_{12}$) and ($C_1$–$C_{13}$)hydrocarbon radicals, in which one to three $CH_2$ groups can be replaced by heteroatoms or heteroatom groups selected from the group consisting of O, $NR^5$ and $SiR^6R^7$, in which $R^5$ is hydrogen, ($C_1$–$C_4$)alkyl or ($C_1$–$C_4$)acyl, and $R^6$ and $R^7$, which are identical or different, independently of one another are ($C_1$–$C_4$)alkyl, phenyl or substituted phenyl, and, moreover, 3 to 8 carbon atoms and, if appropriate, heteroatom radicals of these hydrocarbon radicals, can form a ring and these hydrocarbon radicals, can optionally be substituted by one to three—in the case of halogen up to the maximum number of—identical or different radicals selected from the series consisting of halogen, haloalkyl, cycloalkyl, acyl, phenoxy, substituted phenoxy, phenyl, substituted phenyl, phenylthio and substituted phenylthio;

wherein $R^9$, $R^{10}$, and $R^{11}$ are identical or different and are selected from the group consisting of ($C_1$–$C_4$)alkyl, phenyl and substituted phenyl; and $R^{16}$ and $R^{17}$ are identical or different and independently of one another are hydrogen, ($C_1$–$C_6$)alkyl, ($C_1$–$C_6$)alkoxy, ($C_1$–$C_4$)acyl, ($C_3$–$C_6$)cycloalkyl, phenyl and substituted phenyl.

2. A process for the preparation of compounds of the formula 1, as claimed in claim 1, which comprises reacting compounds of the formula 2

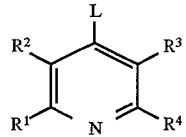

in which $R^1$, $R^2$, $R^3$ and $R^4$ are as defined in claim 1, and L is a leaving group, with suitable amines, alcohols, phenols or mercaptans, or, forming compounds of the formula 1 in which Z is as defined as in claim 1, hydrogenating those compounds of the formula 1 in which $R^1$, $R^2$, $R^3$, $R^4$, X and Y are as defined in claim 1 and Z is an unsaturated carbocyclic radical which is substituted as defined for cycloalkyl or cycloalkenyl in claim 1, and, if appropriate, converting the resulting compounds of the formula 1 into the salt thereof.

3. A method of controlling phytopathogenic fungi, which comprises applying a fungicidally effective amount of a compound as claimed in claim 1, or of a composition containing at least one compound as claimed in claim 1, to these phytopathogenic fungi or to the plants, areas or substrates attacked by them, or to seed.

4. A method of controlling harmful insects, acarina and nematodes, in which an effective amount of a compound as claimed in claim 1, or of a composition containing at least one compound as claimed in claim 1, is applied to these harmful insects, acarina and nematodes or to the plants, areas or substrates attacked by them.

5. Seed, treated or coated with an effective amount of a compound as claimed in claim 1, or of a composition containing at least one compound as claimed in claim 1, and at least one formulation auxiliary.

* * * * *